(12) United States Patent
Fields et al.

(10) Patent No.: US 12,564,464 B2
(45) Date of Patent: Mar. 3, 2026

(54) SURGICAL DRAPING SYSTEM AND METHOD

(71) Applicant: Warsaw Orthopedic, Inc, Us, IN (US)

(72) Inventors: Robert A. Fields, Memphis, TN (US);
Richard A Hynes, Melbourne Beach, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 569 days.

(21) Appl. No.: 15/923,944

(22) Filed: Mar. 16, 2018

(65) Prior Publication Data

US 2019/0282317 A1 Sep. 19, 2019

(51) Int. Cl.
*A61B 46/20* (2016.01)

(52) U.S. Cl.
CPC ........ *A61B 46/20* (2016.02); *A61B 2046/205* (2016.02)

(58) Field of Classification Search
CPC ......... A61B 46/00; A61B 46/20; A61B 46/23; A61B 46/30; A61B 2046/236; A61B 2046/205; A61B 2046/201; A61B 2017/00889; A61F 2013/15073; A61F 2013/00089; A61F 13/15; A61G 13/10; A61G 13/102; A61G 13/107; A61G 17/06; A61G 7/0502; A61G 7/0501; A61G 10/005; A47C 21/024
USPC .......................................... 128/853, 854, 856
See application file for complete search history.

(56) References Cited

U.S. PATENT DOCUMENTS

| | | | | |
|---|---|---|---|---|
| 3,060,932 A | * | 10/1962 | Pereny ................... | A61B 46/00 |
| | | | | 206/440 |
| 3,466,439 A | * | 9/1969 | Edvard ................... | A61B 6/08 |
| | | | | 378/68 |
| 3,968,792 A | | 7/1976 | Small | |
| 4,275,719 A | * | 6/1981 | Mayer ................... | A61B 90/40 |
| | | | | 128/849 |
| 4,350,246 A | | 9/1982 | Mayer | |

(Continued)

FOREIGN PATENT DOCUMENTS

| | | | |
|---|---|---|---|
| CN | 102596089 A | | 7/2012 |
| CN | 203777243 U | * | 8/2014 |

(Continued)

OTHER PUBLICATIONS

International Search Report and Written Opinion for PCT/US2019/022421 the counterpart application mailed on Jul. 2, 2019, 11 pages.

(Continued)

*Primary Examiner* — Alireza Nia
*Assistant Examiner* — Michael Milo
(74) *Attorney, Agent, or Firm* — Sorell, Lenna & Schmidt, LLP

(57) ABSTRACT

A surgical drape includes at least one deployment member connected with draping movable between a non-deployed orientation and a deployed orientation to define a sterile region about a body disposed with a surgical table. The draping includes a first draping and a second draping. A sleeve includes a seal connectable with a selected surface of the body. The sleeve is connectable between the first draping and the second draping to define a sterile passageway including the selected surface. Surgical instruments, systems and methods are disclosed.

20 Claims, 25 Drawing Sheets

(56) References Cited

U.S. PATENT DOCUMENTS

| | | | | |
|---|---|---|---|---|
| 4,905,710 | A | | 3/1990 | Jones |
| 5,417,225 | A | | 5/1995 | Rubenstein et al. |
| 5,433,221 | A | | 7/1995 | Adair |
| 5,523,581 | A | | 6/1996 | Cadwalader |
| 5,649,550 | A | * | 7/1997 | Crook ................ A61B 17/0293 |
| | | | | 128/853 |
| 5,676,159 | A | | 10/1997 | Navis |
| 5,797,403 | A | * | 8/1998 | DiLorenzo ............. A61B 90/40 |
| | | | | 128/849 |
| 5,860,420 | A | * | 1/1999 | Wiedner ................ A61B 46/00 |
| | | | | 128/853 |
| 6,278,125 | B1 | | 8/2001 | Belek |
| 7,604,007 | B1 | | 10/2009 | Wooley |
| 8,807,138 | B2 | | 8/2014 | Byers et al. |
| 9,176,487 | B2 | | 11/2015 | Sperling et al. |
| 2002/0109107 | A1 | | 8/2002 | Goldstein |
| 2003/0205233 | A1 | | 11/2003 | Aboul-Hosn et al. |
| 2006/0021621 | A1 | * | 2/2006 | Kriek .................... A61B 42/10 |
| | | | | 128/849 |
| 2008/0216844 | A1 | * | 9/2008 | Olfert et al. ........... A61B 46/10 |
| | | | | 128/856 |
| 2012/0097176 | A1 | | 4/2012 | Pitaoulis |
| 2013/0101653 | A1 | | 4/2013 | Sperling et al. |
| 2015/0342685 | A1 | | 12/2015 | Livesey |
| 2015/0374442 | A1 | | 12/2015 | Corenman et al. |
| 2016/0120723 | A1 | * | 5/2016 | Giulianotti ........... A61G 10/005 |
| | | | | 600/21 |
| 2016/0135915 | A1 | | 5/2016 | Czajka, Jr. et al. |
| 2017/0119486 | A1 | | 5/2017 | Trauner et al. |
| 2017/0181715 | A1 | * | 6/2017 | Wang et al. ........... A61B 6/032 |
| 2020/0060780 | A1 | * | 2/2020 | Bemman ................ A61B 46/10 |

FOREIGN PATENT DOCUMENTS

| | | |
|---|---|---|
| WO | 1996038096 A1 | 12/1996 |
| WO | 2015117193 A1 | 8/2015 |
| WO | 2015191953 A1 | 12/2015 |
| WO | 2017196566 A1 | 11/2017 |

OTHER PUBLICATIONS

European Patent Office, 80298 Munich, Germany, Extended European Search Report, PCT/US20190224, Mailed Nov. 15, 2021.

* cited by examiner

42

42a                                    42b

50

42c

10

712

752    720    714    718

716

750

714    718    716

752    720

750

782    780

10

SURGICAL DRAPING SYSTEM AND METHOD

TECHNICAL FIELD

The present disclosure generally relates to medical devices for the treatment of musculoskeletal disorders, and more particularly to a surgical draping system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders can include correction, fusion, fixation, discectomy, laminectomy and implantable prosthetics. As part of these surgical treatments, spinal implants including spinal constructs and interbody devices are often used to restore proper alignment and generally support the vertebral members. During surgical treatment, a surgical procedure can employ a surgical drape that covers a patient positioned on a surgical table in an operating room to provide a sterile region. This disclosure describes an improvement over these prior technologies.

SUMMARY

In one embodiment, a surgical drape is provided. The surgical drape includes at least one deployment member connected with draping movable between a non-deployed orientation and a deployed orientation to define a sterile region about a body disposed with a surgical table. The draping includes a first draping and a second draping. A sleeve includes a seal connectable with a selected surface of the body. The sleeve is connectable between the first draping and the second draping to define a sterile passageway including the selected surface. In some embodiments, surgical instruments, systems and methods are disclosed.

In one embodiment, the surgical drape includes a first deployment loop and a second deployment loop. The deployment loops are connected with draping movable between a non-deployed orientation such that the draping includes a rolled configuration and a deployed orientation to define a sterile region about a body disposed with a surgical table. The draping includes a first draping and a second draping. A sleeve includes a seal connectable with a selected surface of the body. The sleeve is expandable between the first draping and the second draping to define a sterile passageway including the selected surface.

In one embodiment, the surgical drape includes a first draping connected with deployment loops and movable between a non-deployed orientation and a deployed orientation to define a sterile region about a body disposed with a surgical table. A sleeve is integrally connected with the first draping and includes a seal connectable with a selected surface of the body. A second draping is connected with deployment loops and movable between a non-deployed orientation and a deployed orientation. The sleeve is attachable with the second draping and disposable between the first draping and the second draping to define a sterile passageway including the selected surface.

BRIEF DESCRIPTION OF THE DRAWINGS

The present disclosure will become more readily apparent from the specific description accompanied by the following drawings, in which.

DETAILED DESCRIPTION

Figure 1:
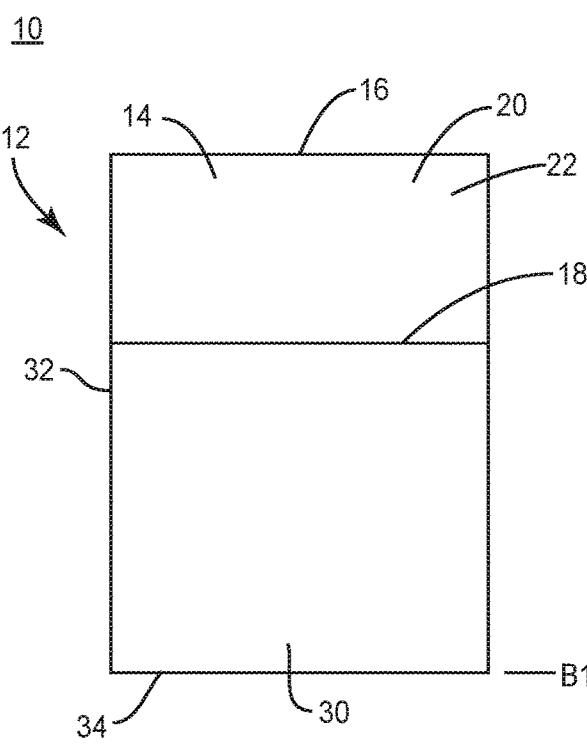
FIG. 1 is a plan view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical draping system and method for treating a spine. In some embodiments, the systems and methods of the present disclosure comprise medical devices that establish and maintain a sterile surgical field with a patient and are employed with a surgical treatment of a cervical, thoracic, lumbar and/or sacral region of a spine. In some embodiments, the present disclosure includes a surgical draping system disposed about a patient and employed with a surgical table such that the patient can be rotated intra-operatively while maintaining a sterile surgical field. See also, the examples and disclosure of a surgical drape system, its components and methods shown and described in commonly owned and assigned U.S. patent application Ser. No. 15/923,973 filed Mar. 16, 2018, and published as U.S. Patent Application Publication No. US-2019-0282329-A1, on Sep. 19, 2019, the entire contents of which being incorporated herein by reference.

In some embodiments, the present system comprises a surgical drape for angular rotation of a patient during spine surgery. In some embodiments, the present system comprises a telescoping surgical drape. In some embodiments, the present system comprises an adhesive sterile tube drape for use with a single-pedestal surgical table. In some embodiments, the surgical drape includes a rail-mounted applicator that applies the drape circumferentially around a patient. In some embodiments, the surgical drape is employed with a single-post surgical table. In some embodiments, the surgical drape is employed with a surgical table such that a patient is rotatable in a range of 0 through 360 degrees without breaking sterility. In some embodiments, the surgical drape can be applied circumferentially around a patient to maintain a sterile field while the patient is rotated 360 degrees intra-operatively via a surgical table. In some embodiments, the surgical drape can be employed with spinal procedures including a rotating surgical table such that surgeons can access any part of a spine from different aspects of the patient. In some embodiments, the surgical drape is movable between a non-deployed orientation and a deployed orientation.

In some embodiments, the present system comprises a surgical drape employed with a surgical table having a single post supporting the table. In some embodiments, the surgical drape includes one or more deployment loops that move along a length of the surgical table. In some embodiments, the deployment loop can have alternate configurations, such as, for example, circular, oval, triangle or rectangular. In some embodiments, the surgical drape encapsulates a patient circumferentially. In some embodiments, the surgical drape includes one or more deployment loops that slide along a rail. In some embodiments, the surgical drape includes tear-away sections to access a surgical site.

In some embodiments, the present system comprises a surgical drape including a loop and draping that is deployed circumferentially using the loop. In some embodiments, the draping is deployed in a 360 degree configuration about the patient. In some embodiments, the draping is attached to the loop. In some embodiments, the draping includes a sterile adhesive drape tube mounted with a loop. In some embodiments, the loop is configured for disposal about a patient. In some embodiments, the loop is connected to a bottom rail of a surgical table. In some embodiments, the surgical drape includes a first loop slidable in a cranial direction and a second loop slidable in a caudal direction. In some embodiments, the surgical drape includes a first loop and a second loop such that the loops are individually and/or separately slidable in a cranial direction and/or a caudal direction from a mid-section of a patient. In some embodiments, the surgical drape includes one or more loops that are slidable via automated movement and/or manual movement via a sterile operator. In some embodiments, the present system is employed with a method including the steps of adhering one portion of an adhesive tube drape to a patient and deploying a loop of the drape in a distal orientation such that the loop is guided away from a starting point aligned with the connection of the drape and the patient.

In some embodiments, the present system comprises a surgical drape having a first loop and a second loop, and is employed with a method including the steps of sterilizing one or more components of the system; disposing the loops adjacent a medial starting point of the loops with the surgical table, the starting point being disposed adjacent a mid-section of a patient; and moving the loops outwardly from the starting point and adhering draping of the surgical drape to the patient as the loops are moved. In some embodiments, the step of sterilizing includes scrubbing a surgical field oriented 360 degrees about a patient. In some embodiments, the loops are pre-loaded with draping. In some embodiments, the loops are slidably movable along a guide rail of a surgical table connected with the surgical drape. In some embodiments, the loops are slidably movable along the guide rail toward a mid-section of a patient. In some embodiments, the draping includes an initial portion that is adhered to a scrubbed surgical field. In some embodiments, the step of moving includes translating the loops away from each other and adhering the draping to the patient during such movement.

In some embodiments, the present system comprises a surgical drape and a surgical table having at least one post that supports a deployment loop of the surgical drape. In some embodiments, the at least one post is engageable and slidable along a track of a rail of the surgical table. In some embodiments, the surgical table includes a first post that supports a first deployment loop and a second post that supports a second deployment loop. In some embodiments, the surgical table includes a waist high sterile barrier drape. In some embodiments, the waist high sterile barrier drape is deployed on both sides of the surgical table. In some embodiments, the waist high sterile barrier drape is attachable to the post and/or the rail. In some embodiments, the waist high sterile barrier protects a portion of the surgical drape that is disposed below a surgeon's belt line.

In some embodiments, the present system comprises a surgical drape including at least one deployment loop having a rigid, circular configuration. In some embodiments, the at least one deployment loop is rigid and includes pre-loaded tube draping. In some embodiments, the at least one deployment loop is attachable with a vertical post of a single-post surgical table that travels along a bottom rail of the surgical table. In some embodiments, the at least one deployment loop is deployable and detachable from the post. In some embodiments, the at least one deployment loop is hinged. In some embodiments, the at least one deployment loop is hinged and opens such that a new, sterile draping can be loaded with the loop. In some embodiments, the at least one deployment loop is reusable and autoclaved. In some embodiments, the at least one deployment loop can be shaped to fit a patient. In some embodiments, the at least one deployment loop is flexible for shaping to fit a patient.

In some embodiments, the present system comprises a surgical drape and a surgical table including a connection mechanism between a drape deployment loop vertical connector and a bottom rail of the surgical table. In some embodiments, the junction facilitates translation along a length of the bottom rail of the surgical table. In some embodiments, the drape is deployed via two deployment loops. In some embodiments, the deployment loops are initially positioned in a middle of the table and translated outwards to the ends of the table into a fully deployed position. In some embodiments, the drape includes standard draping material and an adhesive layer. In some embodiments, a surgeon makes an incision through the applied adhesive layer.

In some embodiments, the present system comprises a drape initially disposed in a rolled up configuration. In some embodiments, the drape is loaded onto a deployment loop. In some embodiments, the drape is unrolled for application to a body of a patient. In some embodiments, as the drape is unrolled, the adhesive portion is adhered to the patient. In some embodiments, the drape is unrolled in a single direction, such as, for example, a caudal direction relative to the patient. In some embodiments, the drape is unrolled in two opposite directions, such as, for example, a caudal and a cranial direction.

In some embodiments, the present system comprises a surgical table including a table support and cushioned patient supports. In some embodiments, the patient supports are configured to facilitate stabilizing the patient during rotation of the table. In some embodiments, the patient supports are positioned to provide unencumbered access to an abdominal region of the patient. In some embodiments, the patient supports are positioned adjacent a thigh and/or a shoulder of the patient. In some embodiments, the drape is configured to maintain a sterile field while the surgical table is rotated. Rotation of the surgical table provides the surgeon with different access approaches to the spine. In some embodiments, the present system avoids having to break down the sterile region during rotation of the surgical table. In some embodiments, the present system provides for use of one drape during a surgical procedure during rotation of the patient.

In some embodiments, the present surgical draping system includes a multi-layer drape. In some embodiments, the layers are connected by a fabric and/or polymeric tube that joins a top surface of an under-layer and a bottom surface of a top-layer. In some embodiments, the connecting layer is disposed about an opening of the two layers. In some embodiments, the multiple layers are configured to maintain the sterile field when the patient is rotated at least 90 degrees.

In some embodiments, the present surgical draping system includes an outer-most layer configured to remain stationary while the table and patient are rotated. In some embodiments, the outer-most layer is connected with a patient-contacting layer. In some embodiments, the patient-contacting layer is configured to be adhered to the patient and rotates with the patient. In some embodiments, the present surgical draping system includes a member that connects the outer-most layer and the patient-contacting layer such that the outer-most layer remains stationary when the patient-contacting layer rotates. In some embodiments, maintaining a stabile top layer provides a surface for placement of tools and other equipment as the table is rotated such that the tools and other equipment do not need to be removed from the top layer during rotation. In some embodiments, the top layer is attached to deployment loop(s) to facilitate stabilizing the top layer. In some embodiments, the present surgical draping system may include two or more layers.

In some embodiments, the present surgical draping system includes a retractor system configured for attachment to the surgical table. In some embodiments, the retractor system is attachable with a top surface of a bottom-most layer and underneath a surface of a top-most layer during rotation. In some embodiments, the present surgical draping system an outermost layer configured to be draped over a Mayo stand to provide additional stability and a place for tools to sit.

In some embodiments, the present surgical draping system includes deployment loops configured to facilitate hands-free deployment of the surgical draping system. In some embodiments, an adhesive seal is adhered to the patient and the deployment loops are translated automatically away from the deployment site, unrolling and deploying the drape. In some embodiments, the deployment loops are translated in different configurations, such as, for example, from the middle outwards towards the head and the feet.

In some embodiments, the present surgical draping system is applied circumferentially around the patient and is configured to maintain patient warmth during use. In some embodiments, the drape is configured to trap heat between the drape and the patient. In some embodiments, the drape may include an insulation material disposed with the patient-contacting layer for warmth.

In some embodiments, the present surgical draping system is configured for use with various types of surgical tables, such as, for example, single-support, dual-support and/or pedestal surgical tables. In some embodiments, the present surgical draping system is configured for use in conjunction with a standard spine drape used in spine surgery. In some embodiments, the standard spine drape is configured to be applied over a fully deployed drape such that the aperture of the standard spine drape is directly over an incision and the seal. In some embodiments, the standard spine drape would be held by IV poles at each of its four corners such that when the table is rotated, the drape rotates with the table because it is adhered to the patient, and the standard spine drape remains stationary. In some embodiments, the aperture of the standard spine drape is configured to remain stationary over the top of the seal, which corresponds to the sterile surfaces of the patient. In some embodiments, the surgeon can operate through the aperture of the standard spine drape by making an incision through the seal when the patient is rotated into an orientation of a desired surgical approach.

In some embodiments, the present surgical draping system includes a section, such as, for example, a pocket configured for disposal of a control mechanism for operation of the surgical table. In some embodiments, the drape includes a clear pocket configured to facilitate sterile access to a table control mechanism by practitioners for manipulation of the controls without breaking sterility. In some embodiments, surgical tables are operated by a handheld remote control that is connected to the table via a cord that is generally disposed in a non-sterile region. As such, if the procedure requires the surgeon to change the position of the table, a non-sterile member of the team is utilized to actuate the controls. In some embodiments, the pocket provides for access to the remote control through the drape. In some embodiments, the pocket is configured to facilitate connection with other devices by touch screen and/or blue tooth.

In some embodiments, the present surgical draping system includes an iPad control screen to provide pressure measurements. In some embodiments, the present surgical draping system includes a device configured for communication with other devices in the operating room, such as, for example, x-rays, C-arms, fluoroscopy, O-arm and/or navigation technology.

In some embodiments, the present surgical draping system maintains a sterile surgical field with a patient during articulation of a patient. In some embodiments, the present surgical draping system maintains a sterile surgical field with a patient to provide simultaneous access to a plurality of surgical pathways and/or approaches, as described herein and for example, a posterior portion of a patient and a lateral portion of the patient accessed during one or more spinal procedures. In some embodiments, the present surgical draping system maintains a sterile surgical field with a patient to provide simultaneous access to an anterior portion of the patient and a lateral portion of the patient accessed during one or more spinal procedures. In some embodiments, the present surgical draping system provides simultaneous access to a plurality of surgical pathways and/or approaches in connection with simultaneous access to vertebral tissue at a surgical site via the plurality of surgical pathways and/or approaches. In some embodiments, the present surgical draping system provides simultaneous access to a plurality of surgical pathways and/or approaches in connection with sequential access to vertebral tissue at a surgical site.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone, lateral or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and iliac regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system and related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-15, there are illustrated components of a surgical system 10.

The components of surgical system 10 can be fabricated from biologically acceptable materials suitable for medical applications. For example, the components of surgical system 10, individually or collectively, can be fabricated from materials such as super-elastic titanium alloys, superelastic metallic alloys (e.g., Nitinol, super elasto-plastic metals, such as GUM METAL®), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene or epoxy.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical draping system 10 may be monolithically formed, integrally connected or include fastening elements and/or instruments, as described herein.

Surgical system 10 may be employed, for example, with minimally invasive procedures, including percutaneous techniques, mini-open surgical techniques and/or open surgical techniques to establish and maintain a sterile surgical field with a patient in connection with a surgical treatment of a spine. In some embodiments, the components of surgical system 10 are employed in connection with surgical treatment that includes access to a surgical site by one or a plurality of surgical approaches. For example, the components of surgical system 10 can be employed with spinal procedures that include access during a single procedure and/or simultaneous access to one or a plurality of surgical approaches and/or surgical pathways including one or more incisions within a sterile boundary. In some embodiments, during a surgical procedure, a patient is disposed with a surgical table that can articulate, orient, position, reposition and/or manipulate the patient for alignment with one or a plurality of surgical approaches. The components of surgical system 10 maintain sterility during such movement of the patient within an enclosed surgical field and/or boundary, for example, during angular rotation of a patient for alignment with one or a plurality of surgical approaches, as described herein. The surgical procedure can include surgical treatment of a cervical, thoracic, lumbar and/or sacral region of a spine.

Figure 19:
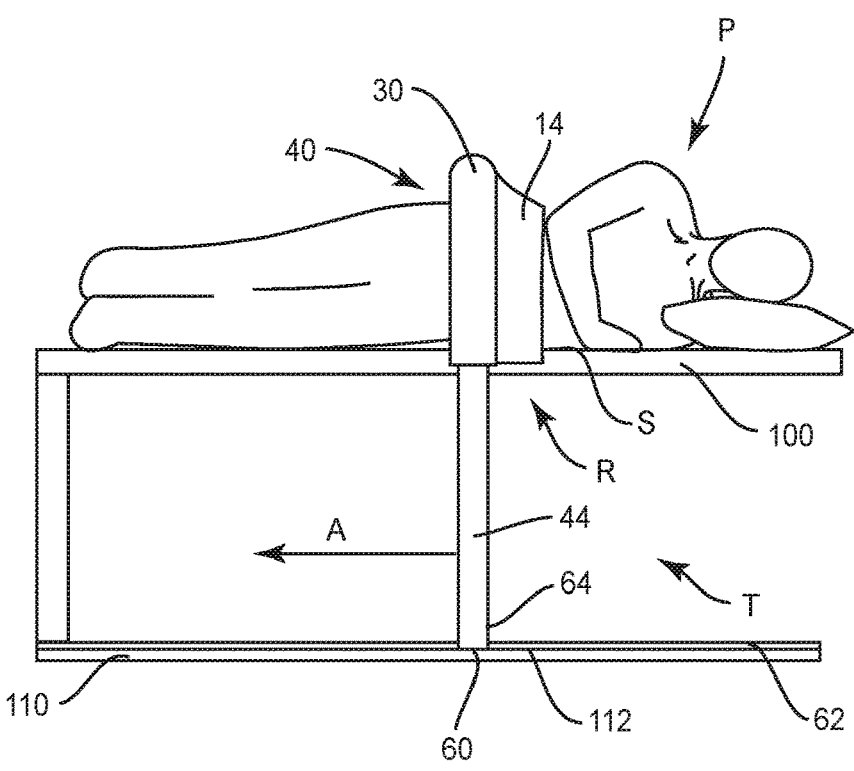
FIG. 19 is a side view of components of one embodiment of a surgical system in accordance with the principles of the present disclosure disposed with a patient body.
Figure 20:
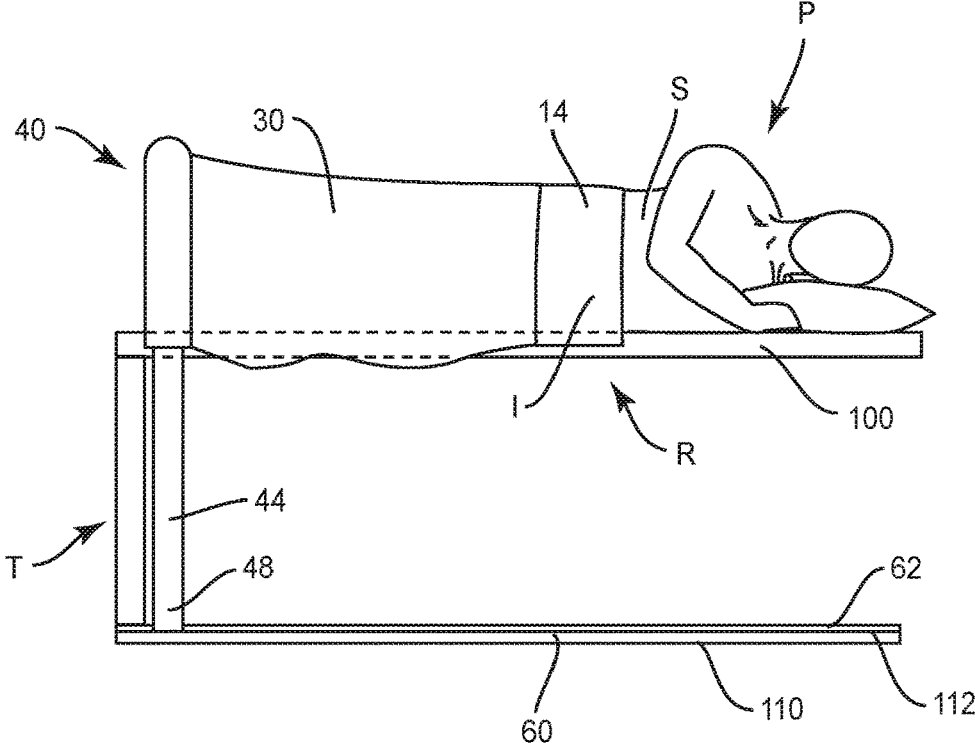
FIG. 20 is a side view of components of one embodiment of a surgical system in accordance with the principles of the present disclosure disposed with a patient body.

Surgical system 10 includes a surgical drape 12. Surgical drape 12 is configured for telescopic deployment to circumferentially enclose a patient P in connection with a surgical treatment of a spine, as described herein. Surgical drape 12 includes a portion, such as, for example a seal 14 and a portion, such, as for example, a draping 30. Seal 14 is configured to adhere to a surface S of a body of patient (FIGS. 19 and 20). Seal 14 includes a flexible configuration such that seal 14 is malleable for attachment with surface S of patient P. Seal 14 extends between an end 16 and an end 18. Seal 14 includes a surface 20 configured for direct engagement with surface S of patient P. In some embodiments, seal 14 includes an anti-microbial incise drape. In some embodiments, surface 20 includes a planar configuration to facilitate attachment with surface S. In some embodiments, surface 20 is coated with a substrate 22. In some embodiments, substrate 22 is applied to surface 20. In some embodiments, substrate 22 includes a pressure-sensitive material that facilitates adherence of seal 14 when applied to surface S. Seal 14 is directly adhered to the skin of patient P. In some embodiments, seal 14 includes an adhesive strip.

In some embodiment, substrate 22 includes a bio-compatible, acrylic adhesive. In some embodiments, substrate 22 includes a soft acrylate adhesive or a silicone gel adhesive. In some embodiments, substrate 22 can be stretchable to facilitate manipulation of seal 14 on surface S. In some embodiments, substrate 22 includes a covering, such as, for example, a peel off layer to facilitate maintaining a sterile surface. In some embodiments, substrate 22 is configured to be removed from the skin of patient P without damage thereto and without causing pain.

Seal 14 is connected and/or adhered to surface S during an initial preparation of a sterile surgical site. For example, substrate 22 is configured to fix seal 14 to surface S such that substrate 22 is configured to resist and/or prevent disengagement of seal 14 from surface S during rotation of patient P. Adherence of seal 14 with surface S allows seal 14 to rotate with the body of patient P as surgical table T is rotated.

Attachment of seal 14 with surface S allows surgical system 10 to maintain sterile region R during rotation of patient P, as described herein. Rotation of the body of patient P provides access to one or more surgical approaches.

Surgical drape 12 includes draping 30. Draping 30 extends between an end 32 and an end 34. End 32 is connected to end 18 of seal 14, as shown in FIG. 1. In some embodiments, draping 30 is connected with seal 14, such as, for example, with by welding, clips, hooks, adhesives and/or flanges. In some embodiments, draping 30 and seal 14 are monolithically formed. In some embodiments, draping 30 is a separate component from seal 14. In some embodiments, draping 30 is an integral component with seal 14.

Figure 5:
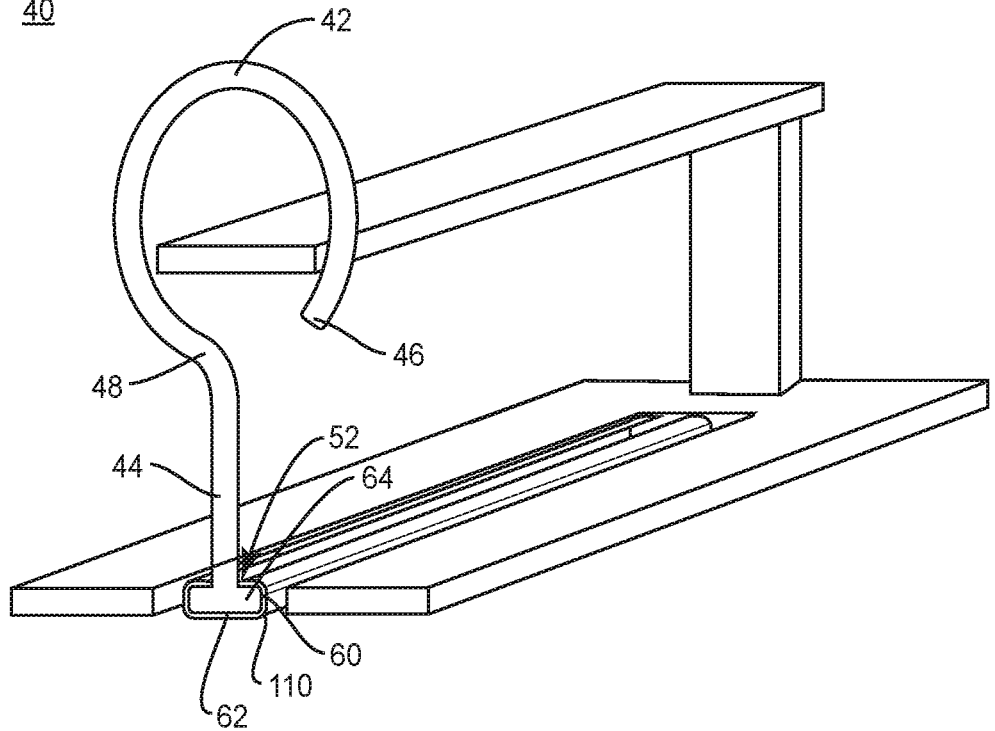
FIG. 5 is a perspective view of components of one embodiment of a surgical system in accordance with the principles of the present disclosure.
Figure 16:
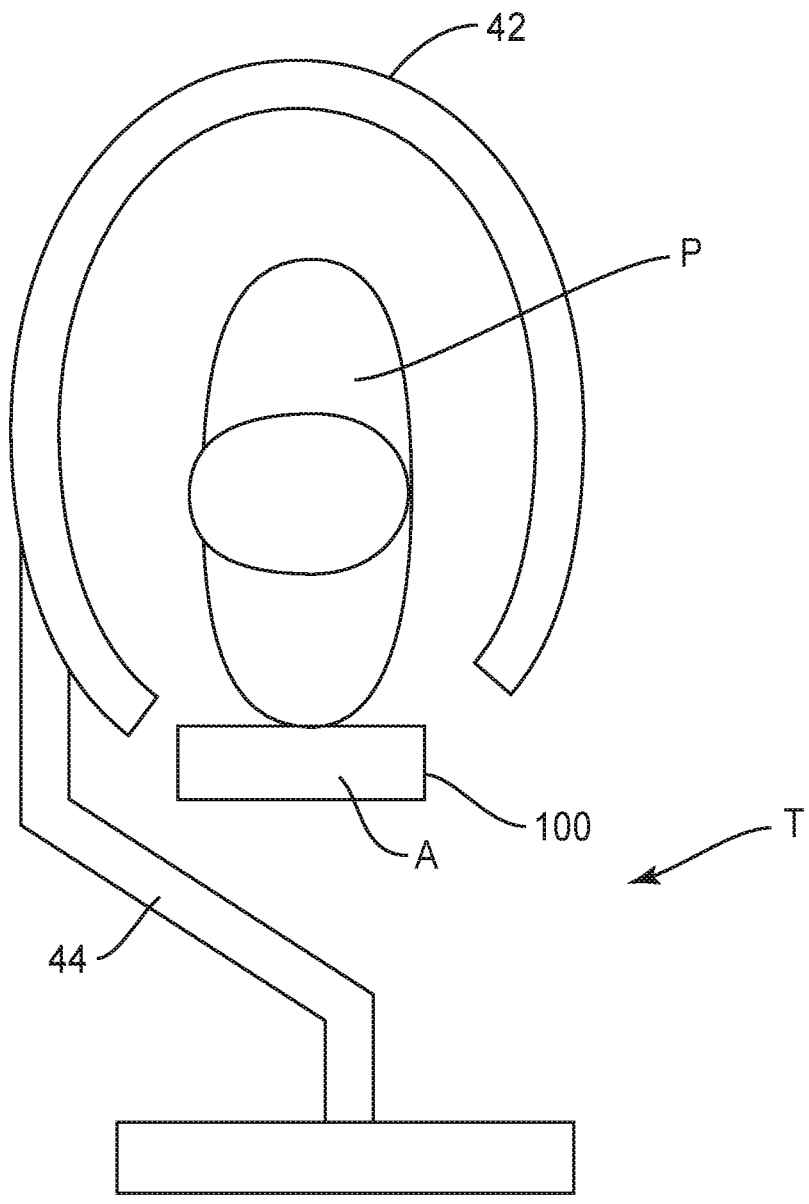
FIG. 16 is a cross section view of components of one embodiment of a surgical system in accordance with the principles of the present disclosure disposed with a patient body.

Surgical drape 12 includes a deployment loop 40, as shown in FIG. 5. Deployment loop 40 includes an arm 42 and a post 44. Arm 42 extends between an end 46 and an end 48. Post 44 extends from arm 42, as shown in FIG. 5. Arm 42 includes an arcuate configuration to facilitate orienting and/or manipulating surgical drape 12 about patient P. Arm 42 disposes surgical drape 12 circumferentially about patient P (FIG. 16). In some embodiments, arm 42 includes a hook configuration to facilitate loading of surgical drape 12 in the non-deployed orientation, as described herein.

Figure 6:
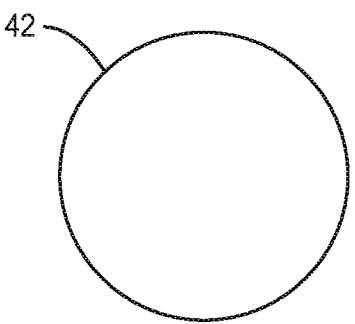
FIG. 6 is a plan view of components of one embodiment of a surgical system in accordance with the principles of the present disclosure.
Figure 7:
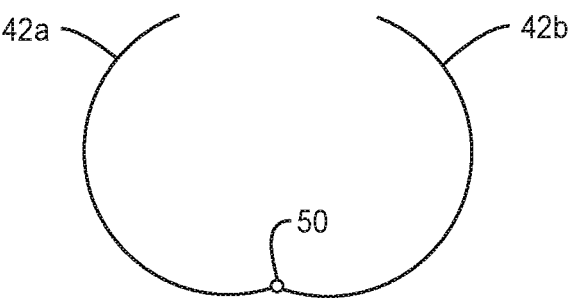
FIG. 7 is a plan view of components of one embodiment of a surgical system in accordance with the principles of the present disclosure.
Figure 8:
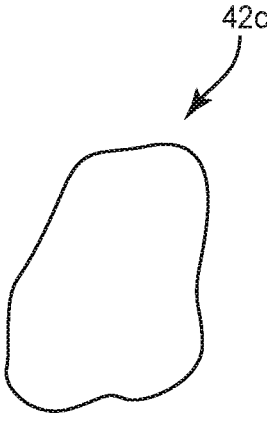
FIG. 8 is a plan view of components of one embodiment of a surgical system in accordance with the principles of the present disclosure.
Figures 9, 10, 11, 12, 13:
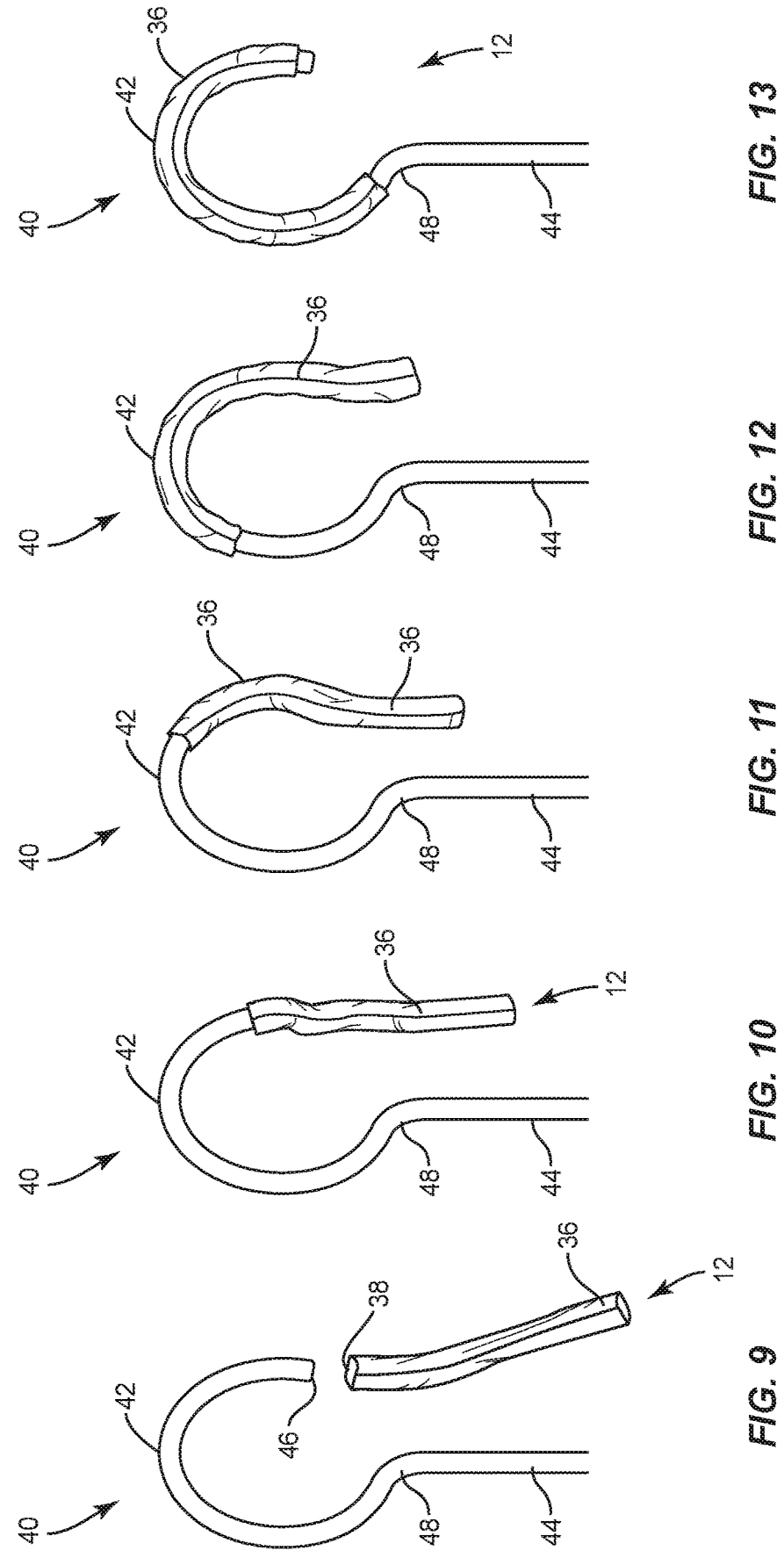
FIG. 9 is a side view of components of one embodiment of a surgical system in accordance with the principles of the present disclosure.
FIG. 10 is a side view of the components shown in FIG. 9.
FIG. 11 is a side view of the components shown in FIG. 9.
FIG. 12 is a side view of the components shown in FIG. 9.
FIG. 13 is a side view of the components shown in FIG. 9.

In some embodiments, arm 42 includes a circular configuration, as shown in FIG. 6. In some embodiments, deployment loop 40 includes an arm 42a and an arm 42b, as shown in FIG. 7. Arm 42a is moveable relative to arm 42b, such as, for example, by a hinge 50. In some embodiments, deployment loop 40 includes a flexible arm 42c, as shown in FIG. 8. In some embodiments, arm 42c is movable and/or malleable to a plurality of orientations to conform to a shape of patient P.

Figure 14:
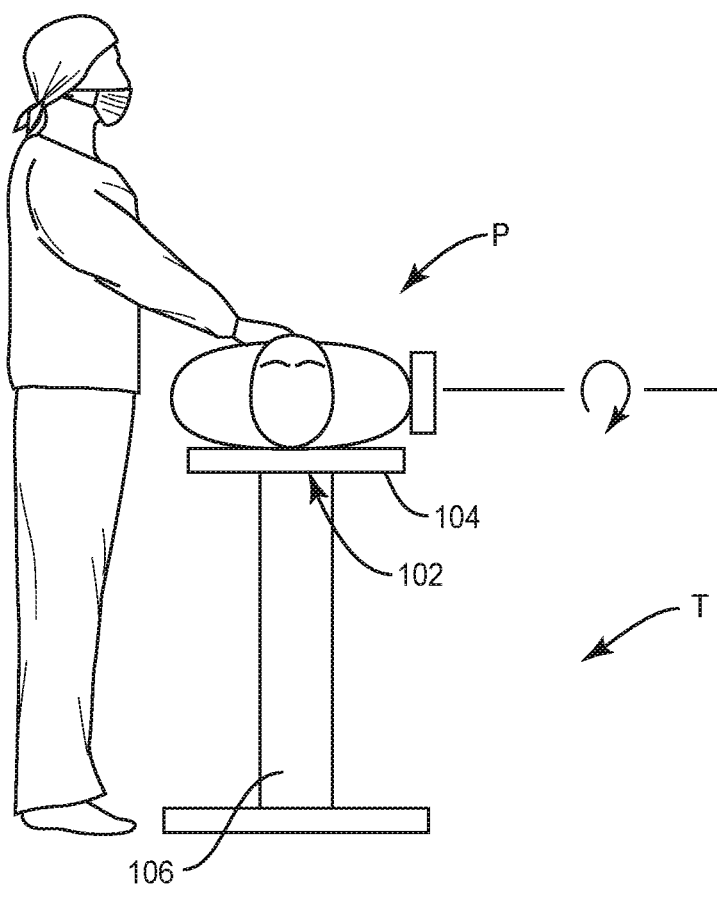
FIG. 14 is a plan view of components of one embodiment of a surgical system in accordance with the principles of the present disclosure disposed with a patient body.
Figure 15:
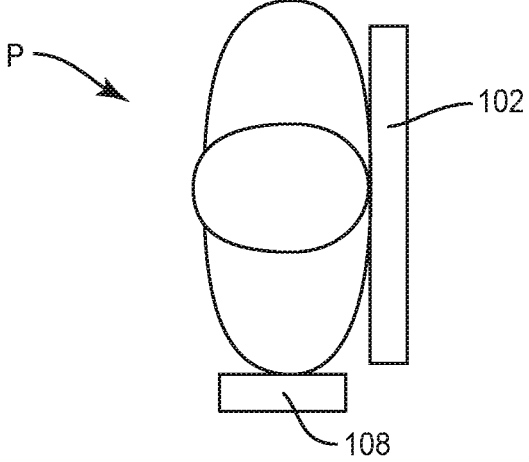
FIG. 15 is a plan view of components of one embodiment of a surgical system in accordance with the principles of the present disclosure disposed with a patient body.

Surgical table T, as shown in FIGS. 14-16 and 19-20, includes a support 100 configured for disposal of patient P. Support 100 is configured to maintain patient P in various orientations, such as, for example, supine, prone or on a side. In some embodiments, support 100 is planar. Support 100 extends between an end 102 and an end 104. Surgical table T is supported by a single pedestal 106, as shown in FIG. 14. Pedestal 106 extends from an end 102 of support 100. Positioning of pedestal 106 at end 102 facilitates translation of draping 30 and deployment loop 40, relative to support 100, by providing free translation and unencumbered passage of deployment loop 40 along support 100. In some embodiments, surgical table T includes a second support 108 configured to facilitate maintaining the position of patient P during rotation of surgical table T, as shown in FIG. 15.

Surgical table T includes a base rail 110 that extends from pedestal 106, as shown in FIGS. 19 and 20. Rail 110 extends along all or a portion of support 100. Rail 110 includes a connecting mechanism for connection of post 44 thereto. Rail 110 includes a surface 112 that defines a slot, such as, for example, a track 60. Track 60 is in open communication with surface 112 to define a track pathway 62. Track pathway 62 facilitates translation of deployment loop 40 and/or surgical drape 12 relative to patient P, as described herein. In some embodiments, track pathway 62 is linear in shape. In some embodiments, all or only a portion of track pathway 62 may have alternate configurations, such as, for example, arcuate, undulating and/or offset.

Post 44 is configured for connection with track 60 via end 52. End 52 includes a t-shaped slider 64 configured to engage track 60, as shown in FIG. 5. Slider 64 is engageable with track 60 for slidable translation of deployment loop 40 and/or surgical drape 12 relative to patient P along track pathway 62. Deployment loop 40 is translated along track pathway 62 causing draping 30 to be manipulated, expanded, drawn and/or translated from the non-deployed orientation to the deployed orientation, as described herein. In some embodiments, a dovetail sliding attachment mechanism can be utilized.

In some embodiments, deployment loop 40 is manually translatable along track 60. In some embodiments, post 44 is connected with end 48, such as, for example, with clips, hooks, adhesives and/or flanges. In some embodiments, post 44 and arm 42 are monolithically formed. In some embodiments, post 44 is a separate component from arm 42. In some embodiments, post 44 is an integral component with arm 42.

Figure 2:
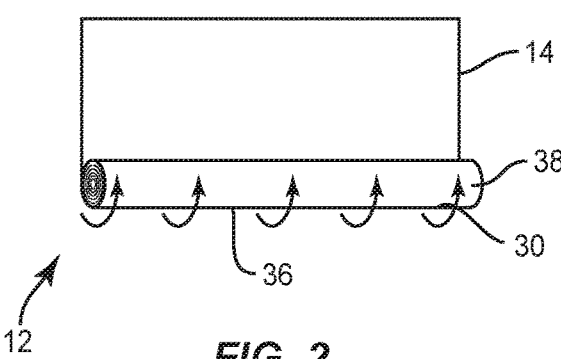
FIG. 2 is a perspective view of components of one embodiment of a surgical system in accordance with the principles of the present disclosure.
Figure 3:
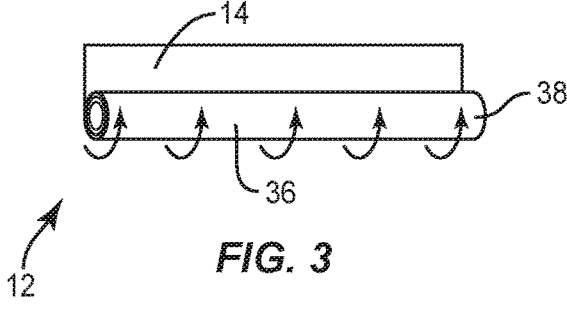
FIG. 3 is a perspective view of the components shown in FIG. 2.
Figure 4:
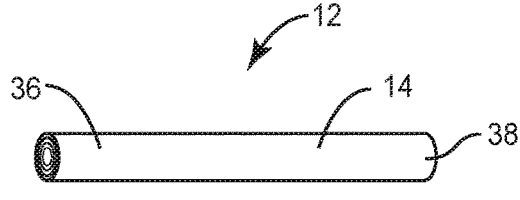
FIG. 4 is a perspective view of the components shown in FIG. 2.
Figures 17, 18:
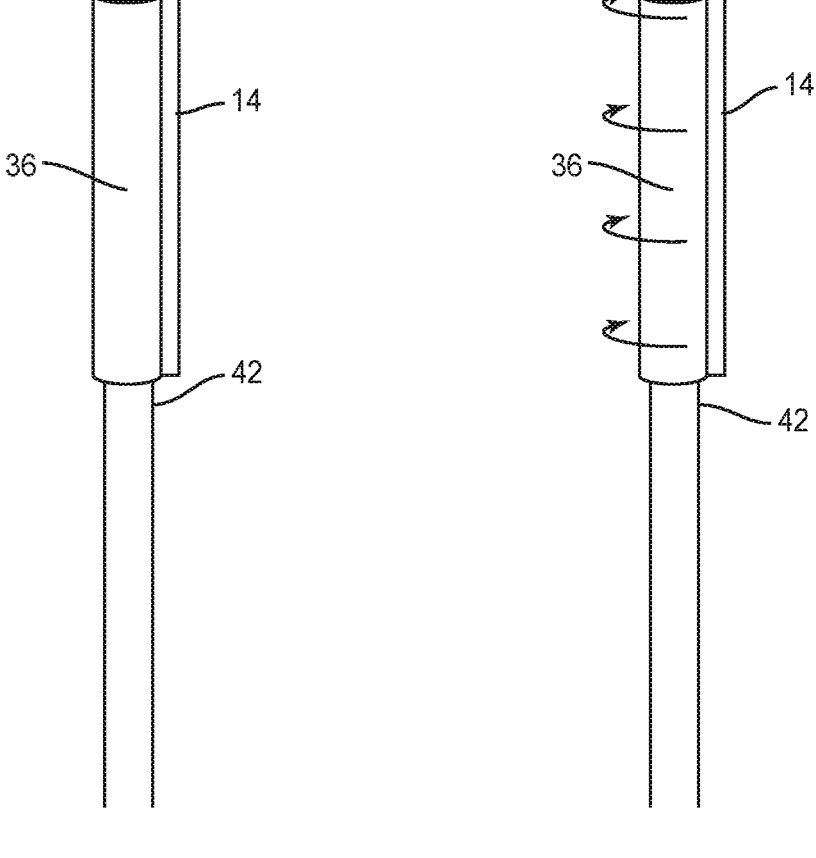
FIG. 17 a perspective view of components of one embodiment of a surgical system in accordance with the principles of the present disclosure.
FIG. 18 is a perspective view of the components shown in FIG. 17.

In operation, draping 30 and seal 14 are configured to be disposed in a non-deployed orientation, as shown in FIG. 17, and manipulated, drawn, expanded and/or translated to a deployed orientation, as shown in FIG. 20, for circumferential disposal about the body of patient P and/or to define a sterile region about the body of patient P. In the non-deployed orientation, drape 12 is disposed in contracted, collapsed and/or compact configuration, such as, for example, a roll 36. For example, end 34 is wound, loaded, rotated, and/or rolled about an axis B1 causing draping 30 and seal 14 to form roll 36. Roll 36 includes a tubular configuration and defines a passageway 38, as shown in FIGS. 2-4. Roll 36 is configured for mounting with deployment loop 40 such that a portion of deployment loop 40 is disposed with passageway 38, as described herein. Roll 36 is disposed with deployment loop 40 and seal 14 can be fixed with surface S such that draping 30 is drawn, expanded and/or translated relative to seal 14 in a telescoping configuration during deployment.

Roll 36 is mounted with arm 42, as shown in FIGS. 9-13. End 46 of arm 42 is positioned with passageway 38. Roll 36 is translated and/or guided along arm 42 such that roll 36 extends along arm 42 to facilitate circumferentially enclosing patient P and defining sterile region R. Seal 14 is adhered to surface S of patient P. With seal 14 fixed with surface S, deployment loop 40 is translated, as described herein, with roll 36 mounted thereon such that deployment loop 40 is translated relative to patient P and along surgical table T. Such translation of deployment loop 40 relative to patient P dispenses draping 30 from roll 36 away from seal 14 to draw, expand and/or translate draping 30 circumferentially about patient P. Draping 30 is telescopically drawn from roll 36 to draw, expand and/or translate draping 30 relative to seal 14 in a circumferential orientation to define sterile region R about the body of patient P.

In assembly, operation and use, as shown in FIGS. 16-20, surgical system 10, similar to the systems and methods described herein, includes surgical drape 12, which is employed in connection with a surgical approach strategy for a surgical procedure to treat one or more spinal disorders.

In connection with the procedure, a surgeon formulates a strategy for surgical treatment including access to a surgical site via one or more selected surgical approaches. In some embodiments, the surgical procedure includes, but is not limited to, surgical treatment of a cervical, thoracic, lumbar and/or sacral region of a spine that may utilize access to a surgical site via one or more surgical approaches. The surgeon can employ surgical system 10 in connection with such access, which may include disposing a patient on surgical table T and articulating, orienting, positioning, repositioning and/or manipulating the patient for alignment with the surgical approaches. In some embodiments, the surgeon defines sterile region R by determining the selected surgical approaches, which may include one or more of anterior, posterior, posterior mid-line, direct lateral, postero-lateral, antero-lateral approaches and/or combinations thereof. In some embodiments, a surgical field including sterile region R is prepared and/or sterilized including one or more components of surgical system 10, patient P and/or about patient P. In some embodiments, a step of sterilizing the surgical field includes scrubbing the surgical field oriented 360 degrees about a patient. See also, the examples and disclosure of surgical sterilization methods shown and described in commonly owned and assigned U.S. patent application Ser. No. 15/923,973 filed Mar. 16, 2018, and published as U.S. Patent Application Publication No. US-2019-0282329-A1, on Sep. 19, 2019; the entire contents of which being incorporated herein by reference; and the examples and disclosure of surgical sterilization systems shown and described in commonly owned and assigned U.S. patent application Ser. No. 15/924,021 filed Mar. 16, 2018, and published as U.S. Patent Application Publication No. US-2019-0282330-A1, on Sep. 19, 2019; the entire contents of which being incorporated herein by reference.

For example, the procedure can include access via a lateral surgical approach and a separate postero-lateral or posterior surgical approach. Surgical drape 12 maintains sterility of a surgical site during rotation, repositioning and/or manipulation of patient P, as described herein. In some embodiments, surgical access can include access and/ or repositioning to a right lateral side portion, a left lateral side portion, an anterior portion and/or a posterior portion of patient P. In some embodiments, surgical access can include access to a posterior portion of a patient P and a lateral side of patient P. In some embodiments, surgical access can include access to an anterior portion of patient P and a lateral side of patient P.

Patient P is positioned on surgical table T, for example, in a lateral position. Surgical table T is mechanically configured to rotate, reposition and/or manipulate patient P in connection with the spinal procedure to provide simultaneous access to the selected surgical approaches and/or vertebral tissue at the surgical site. In some embodiments, surgical table T rotates patient P into alignment with the selected surgical approaches via a 360 angular degree rotation of surgical table T about an axis A, as shown in FIG. 16. In some embodiments, one or more practitioners may physically manipulate patient P for rotation to provide simultaneous access to the selected surgical approaches.

In connection with the selected surgical approaches, for example, the lateral and postero-lateral or posterior surgical approaches, the surgical site, which may include one or more incisions, retracted openings, pathways and/or passageways created with the body of patient P, are identified and/or determined to define sterile region R. For example, sterile region R includes the one or more incisions, retracted openings, pathways and/or passageways aligned with the lateral and postero-lateral or posterior surgical approaches created in the tissue surfaces of patient P disposed within selected tissue surface S, which bounds sterile region R. In some embodiments, sterile region R is established and maintained above a surface of surgical table T. In some embodiments, the space above the surface of surgical table T is considered a sterile region. In some embodiments, the space from surgical table T to the floor is considered a non-sterile region. In some embodiments, the surgical site and/or sterile region R include vertebral tissue.

Roll 36 is mounted with arm 42 of deployment loop 40 in a non-deployed orientation, as shown in FIG. 17 and described herein. Arm 42 is positioned circumferentially about patient P. End 52 of post 44 is engaged with track 60, as described herein. Seal 14 is positioned over the surgical site and adhered to surface S of patient P, as shown in FIG. 19. With seal 14 fixed with surface S, deployment loop 40 is translated, in a direction shown by arrow A in FIG. 19, with roll 36 mounted thereon such that deployment loop 40 is translated relative to patient P and along surgical table T. Such translation of deployment loop 40 relative to patient P dispenses draping 30 from roll 36 away from seal 14 to draw, expand and/or translate draping 30 circumferentially about patient P. Draping 30 is telescopically drawn from roll 36 to draw, expand and/or translate draping 30 relative to seal 14 in a circumferential orientation to define sterile region R about the body of patient P. In some embodiments, deployment loop 40 is translated in a caudal direction. Drape 12 maintains sterility within sterile region R as patient P is rotated in a range of 0 through 360 via surgical table T.

The surgeon can access the surgical site through seal 14, and the surgical procedure is performed including making the one or more incisions I, retracted openings, pathways and/or passageways in the tissue surfaces of patient P within sterile region R. In some embodiments, patient P is initially oriented in a lateral position or rotated by surgical table T from a prone position to a lateral position to provide surgical access via a lateral surgical approach to vertebral tissue within sterile region R. For example, a lateral lumbar interbody graft/cage insertion can be performed via the lateral surgical approach. In some embodiments, patient P is initially oriented in a prone position or rotated by surgical table T from a lateral position to a prone position to provide surgical access via the postero-lateral or posterior surgical approaches to vertebral tissue within sterile region R. For example, implantation of posterior instrumentation or constructs can be performed via the postero-lateral or posterior surgical approaches. In some embodiments, rotation, repositioning and/or manipulation of patient P provides simultaneous access to the selected surgical approaches.

Upon completion of the procedure, the surgical instruments and non-implanted components are removed from the surgical site and the incisions, openings, pathways and/or passageways are closed. One or more of the components of surgical system 10 can be made of radiolucent materials such as polymers. Radiomarkers may be included for identification under x-ray, fluoroscopy, CT or other imaging techniques.

In some embodiments, as shown in FIGS. 21-28, surgical system 10, similar to the systems and methods described herein, includes a drape 212, similar to drape 12 described herein. Surgical drape 212 is configured for bi-directional telescopic deployment of draping to enclose a patient P and provide access to one or more selected surgical approaches in connection with surgical treatment of a spine, as described herein.

Figure 21:
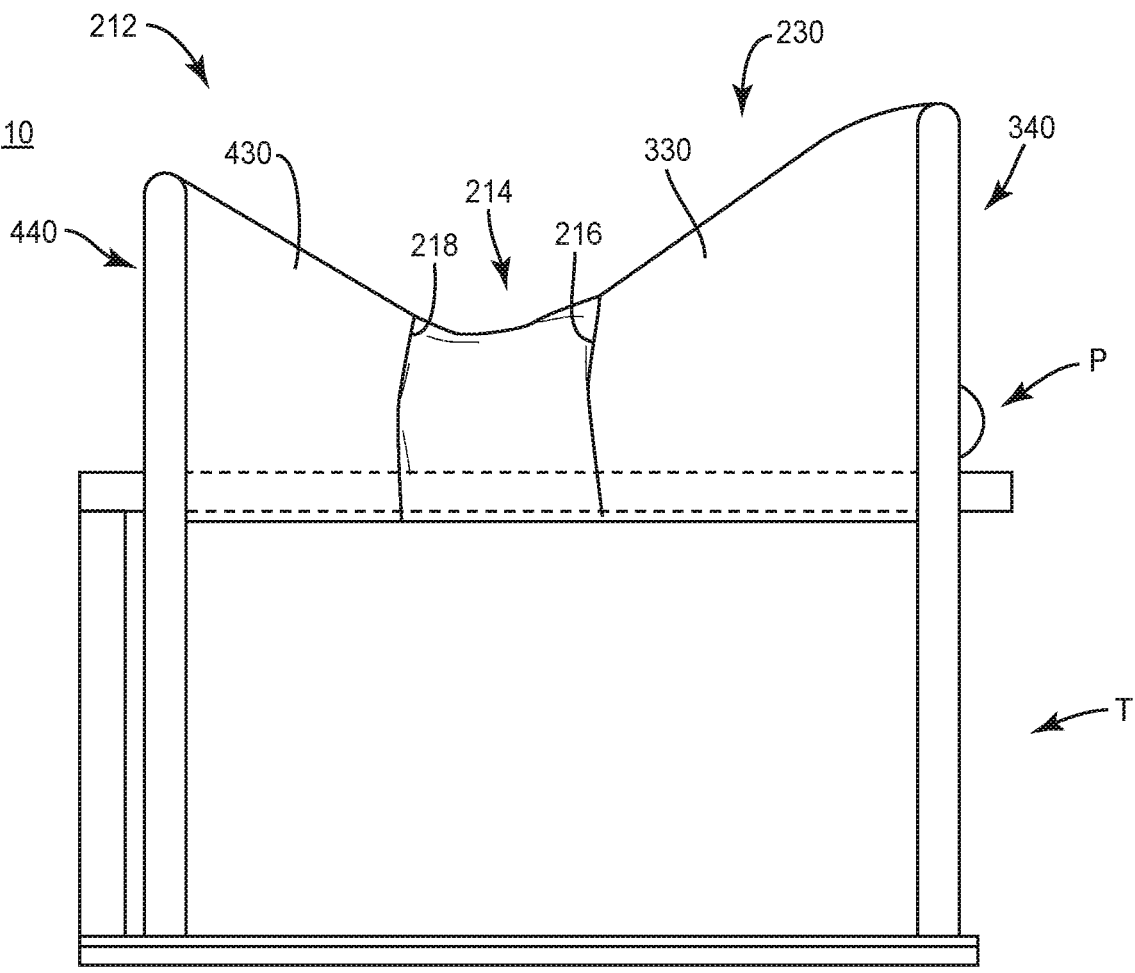
FIG. 21 is a side view of components of one embodiment of a surgical system in accordance with the principles of the present disclosure disposed with a patient body.

Surgical drape 212 includes a portion, such as, for example a seal 214, similar to seal 14 described herein and a portion, such, as for example, a draping 230 similar to draping 30 described herein. Seal 214 is configured to adhere to a surface S of a body of patient, as described herein. Seal 214 is connected and/or adhered to surface S during an initial preparation of a sterile surgical site, as described herein. Draping 230 includes a section 330 and a section 430. Section 330 is connected to an end 216 of seal 214, as shown in FIG. 21. Section 430 is connected to an end 218 of seal 214.

Surgical drape 212 includes a deployment loop 340 attached with section 330 and a deployment loop 440 attached with section 430. Deployment loop 340 includes an arm 342 and a post 344, similar to deployment loop 40 described herein. Deployment loop 440 includes an arm 442 and a post 444, similar to deployment loop 40 described herein. Deployment loops 340, 440 are configured for connection with a surgical table, similar to surgical table T described herein.

Figure 22:
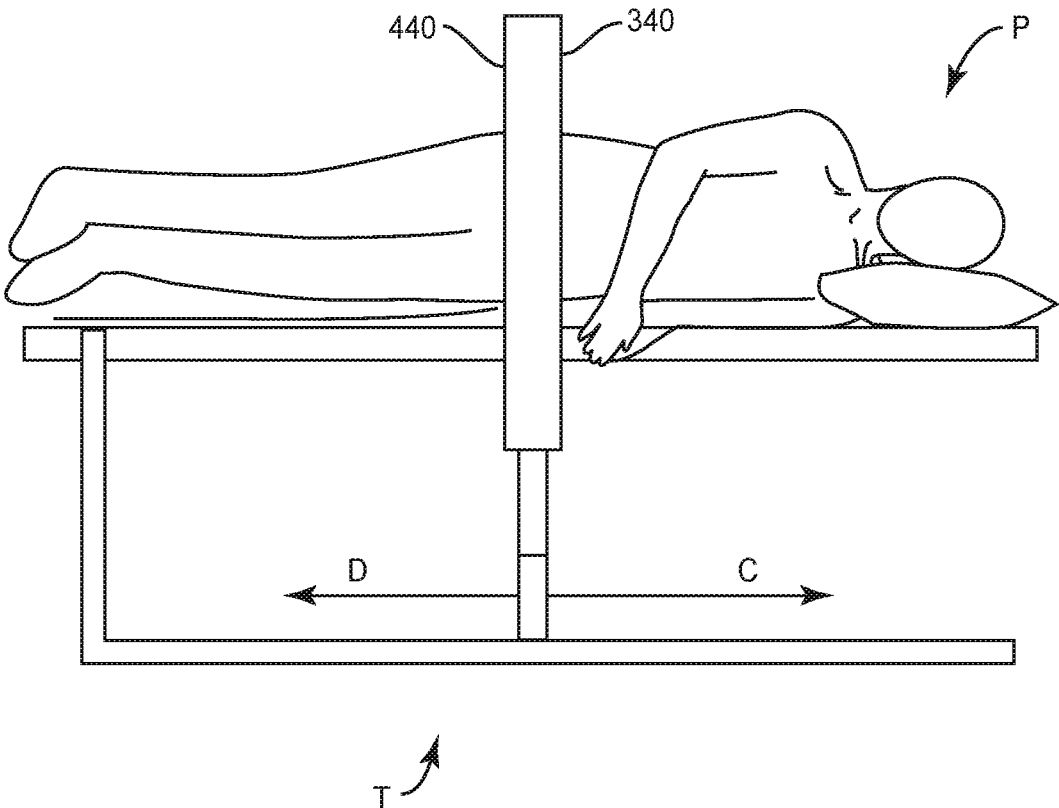
FIG. 22 is a side view of components of one embodiment of a surgical system in accordance with the principles of the present disclosure disposed with a patient body.
Figure 23:
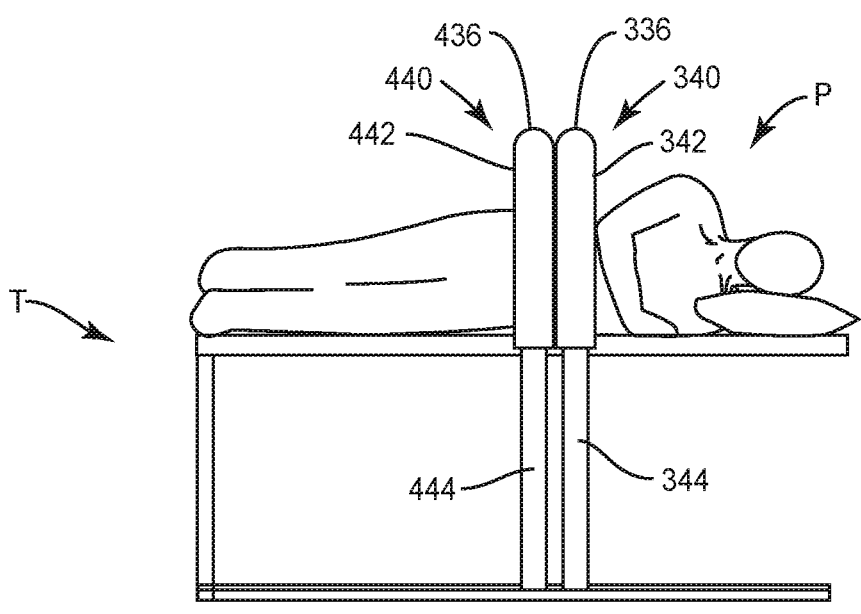
FIG. 23 is a side view of components of one embodiment of a surgical system in accordance with the principles of the present disclosure disposed with a patient body.
Figure 24:
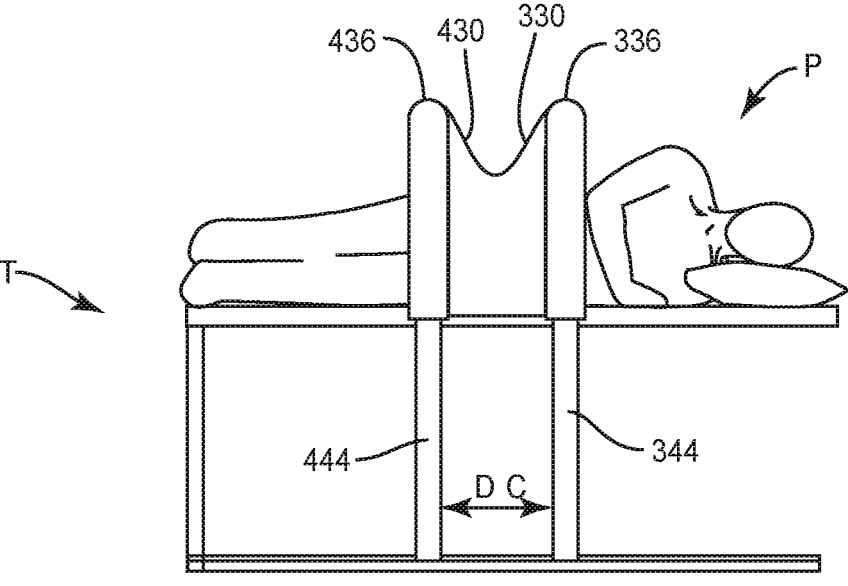
FIG. 24 is a side view of the components and body shown in FIG. 23.
Figure 25:
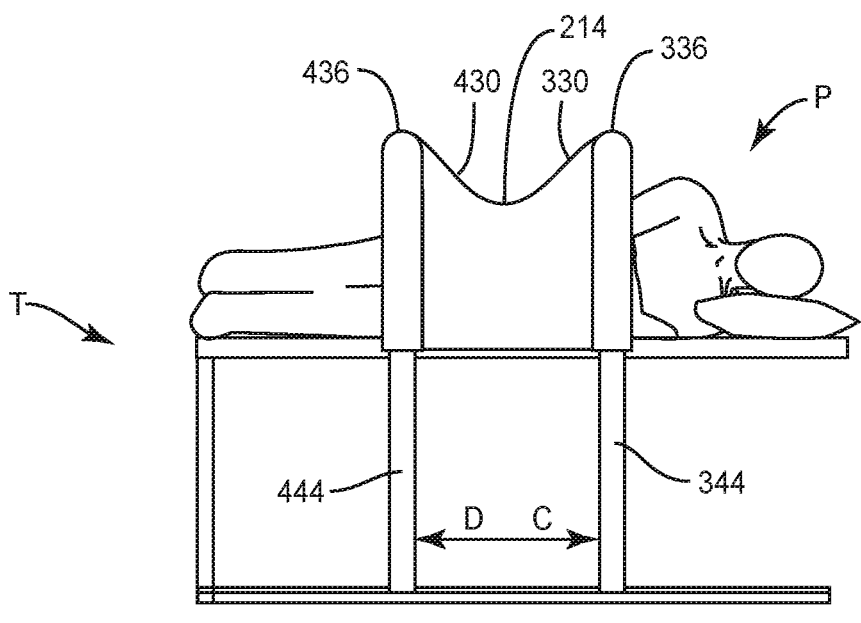
FIG. 25 is a side view of the components and body shown in FIG. 23.
Figure 26:
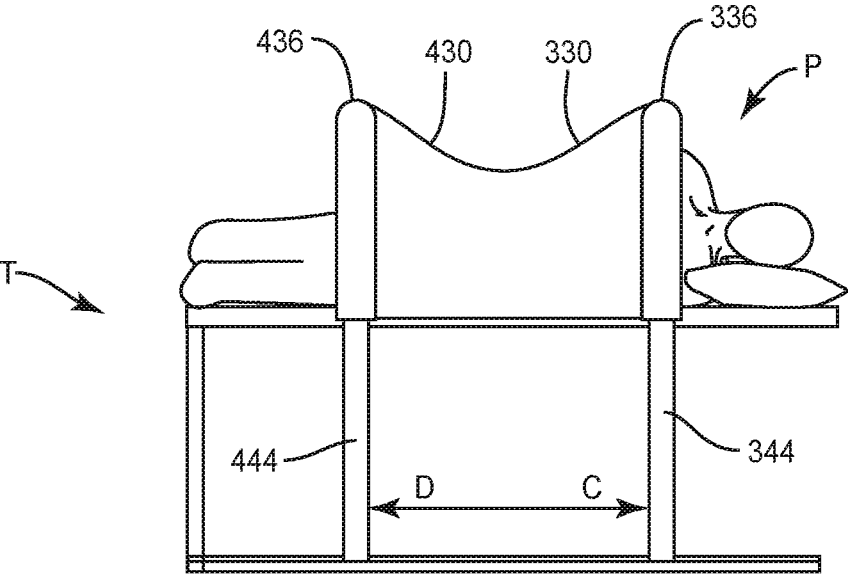
FIG. 26 is a side view of the components and body shown in FIG. 23.
Figure 27:
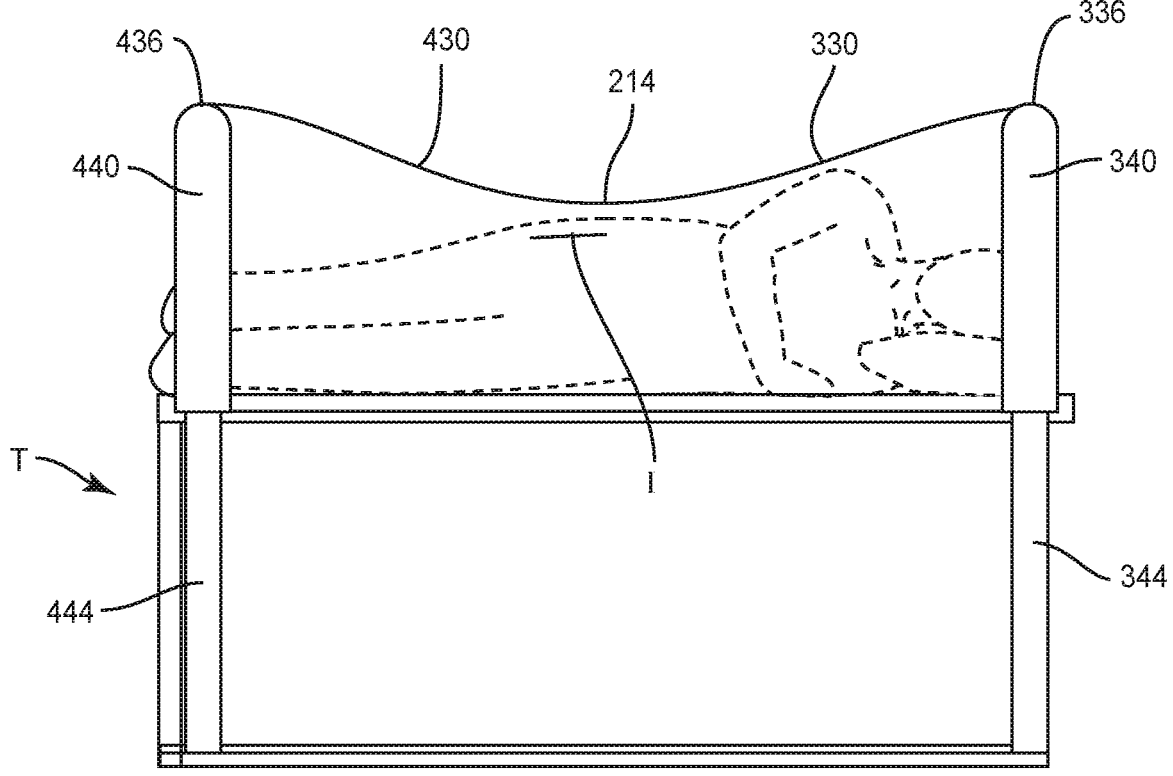
FIG. 27 is a side view of the components and body shown in FIG. 23.
Figure 28:
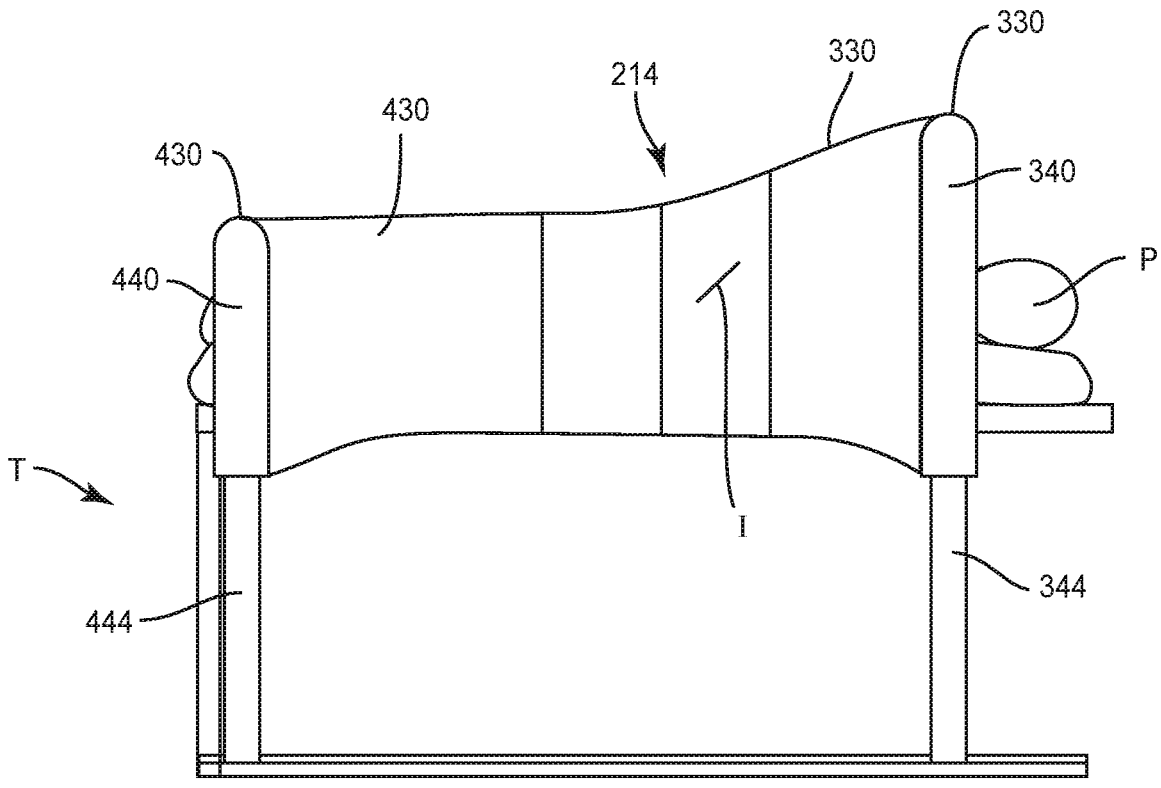
FIG. 28 is a side view of the components and body shown in FIG. 23.

In operation, draping 230 and seal 214 are configured to be disposed in a non-deployed orientation, as shown in FIG. 23, and manipulated, drawn, expanded and/or translated to a deployed orientation, as shown in FIGS. 24-28, for circumferential disposal about the body of patient P and/or to define a sterile region R about the body of patient P. In the non-deployed orientation, drape 212 is disposed in a contracted, collapsed and/or compact configuration, similar to that described with regard to drape 12. For example, section 330 is wound, loaded, rotated and/or rolled to form a roll 336. Section 430 is wound, loaded, rotated and/or rolled to form a roll 436. Deployment loops 340, 440 are disposed about a mid-section of patient P, as shown in FIGS. 22 and 23. Seal 214 is disposed between roll 336 and roll 436, as shown in FIG. 24.

Roll 336 is mounted with deployment loop 340 and roll 436 is mounted with deployment loop 440, similar to that described herein, such that seal 214 is fixed with surface S and draping 230 is drawn, expanded and/or translated relative to seal 214 in a telescoping configuration during deployment. Roll 336 is translated and/or guided along deployment loop 340, similar to that described herein, such that roll 336 facilitates circumferentially enclosing patient P and defining sterile region R. Roll 436 is translated and/or guided along deployment loop 440, similar to that described herein, such that roll 436 facilitates circumferentially enclosing patient P and defining sterile region R. In some embodiments, loop 340 and loop 440 are individually and/or separately slidable in a cranial direction and/or a caudal direction from a mid-section of patient P.

Seal 214 is positioned over the surgical site and adhered to surface S of patient P. With seal 214 fixed with surface S, deployment loop 340 is translated from the mid-section of patient P, in a direction shown by arrow C in FIGS. 22-26, relative to patient P and along surgical table T. In some embodiments, deployment loop 340 is translated in a cranial direction. Such translation of deployment loop 340 relative to patient P dispenses draping 330 from roll 336 away from seal 214 to draw, expand and/or translate draping 330 circumferentially about patient P. Deployment loop 440 is translated from the mid-section of patient P in a direction opposite to that of deployment loop 340, as shown by arrow D in FIGS. 22-26, relative to patient P and along surgical table T. In some embodiments, deployment loop 440 is translated in a caudal direction. Such translation of deployment loop 440 relative to patient P dispenses draping 430 from roll 436 away from seal 214 to draw, expand and/or translate draping 430 circumferentially about patient P.

Figure 29:
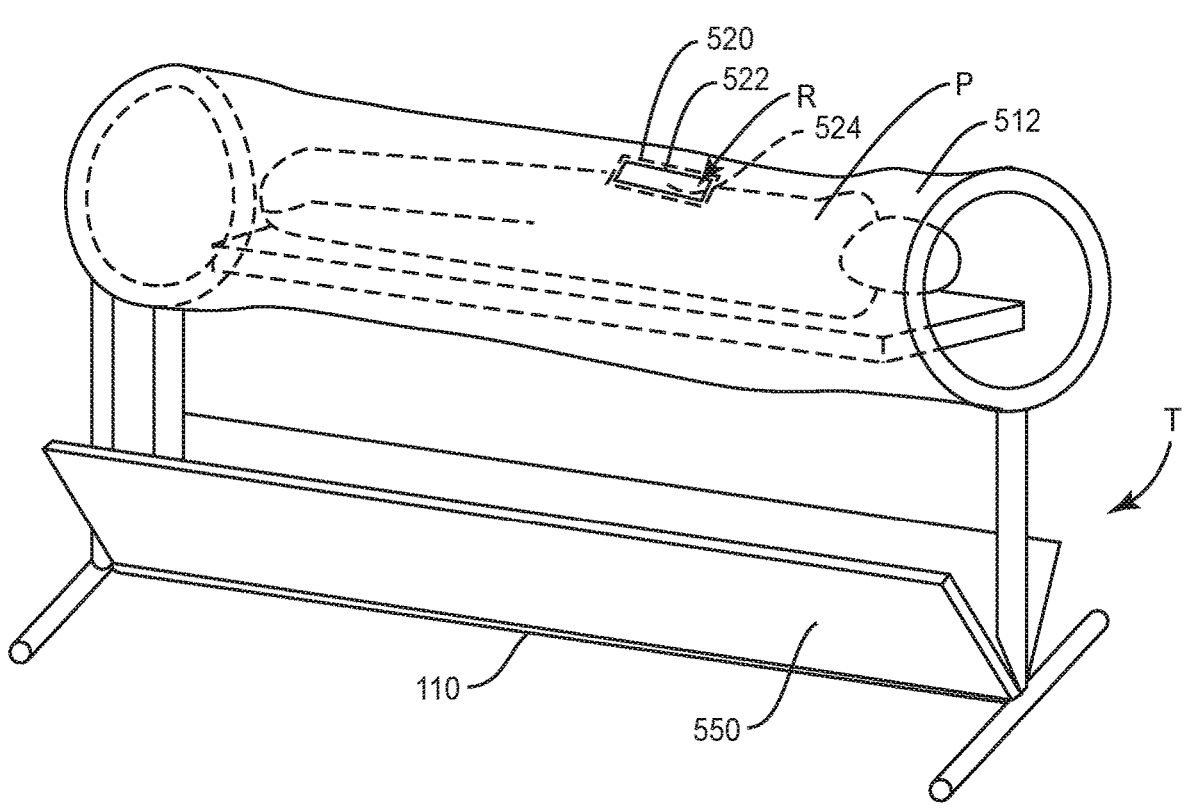
FIG. 29 is a side view of components of one embodiment of a surgical system in accordance with the principles of the present disclosure disposed with a patient body.
Figure 30:
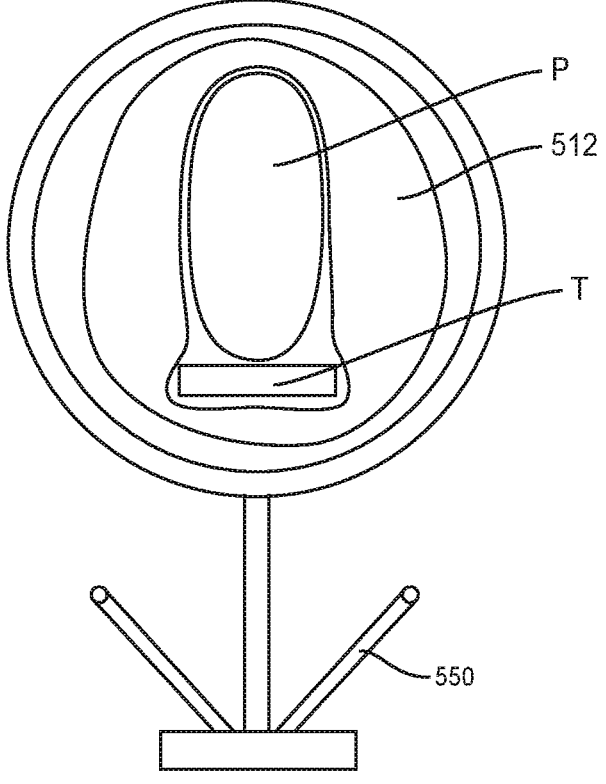
FIG. 30 is an end view of components of one embodiment of a surgical system in accordance with the principles of the present disclosure disposed with a patient body.

In some embodiments, as shown in FIGS. 29 and 30, surgical system 10, similar to the systems and methods described herein, includes a drape 512, similar to drape 12 described herein. Surgical drape 512 is configured for telescopic deployment of draping to enclose a patient P and portions of table T, and provide access to one or more selected surgical approaches in connection with surgical treatment of a spine, as described herein.

Drape 512 includes a surface 520 that defines an opening 522. Opening 522 is configured to provide access to a surgical region R, as described herein. In some embodiments, drape 512 includes a moveable panel, such as, for example, a tear away panel 524 configured to provide access to sterile region R through opening 522 of drape 512.

In some embodiments, surgical system 10 includes a sterile barrier 550 employed in connection with drape 512, which encloses patient P and a platform of table T that supports patient P. Sterile barrier 550 is connected with rail 110 of surgical table T, such as, for example, by clips, hooks, adhesives and/or flanges. In some embodiments, sterile barrier 550 extends to a waist height of a practitioner. In some embodiments, sterile barrier 550 extends to a hip height of a practitioner. In some embodiments, sterile barrier 550 extends along both sides of surgical table T. In some embodiments, sterile barrier 550 is disposable and changed for a new surgical procedure.

Figure 31:
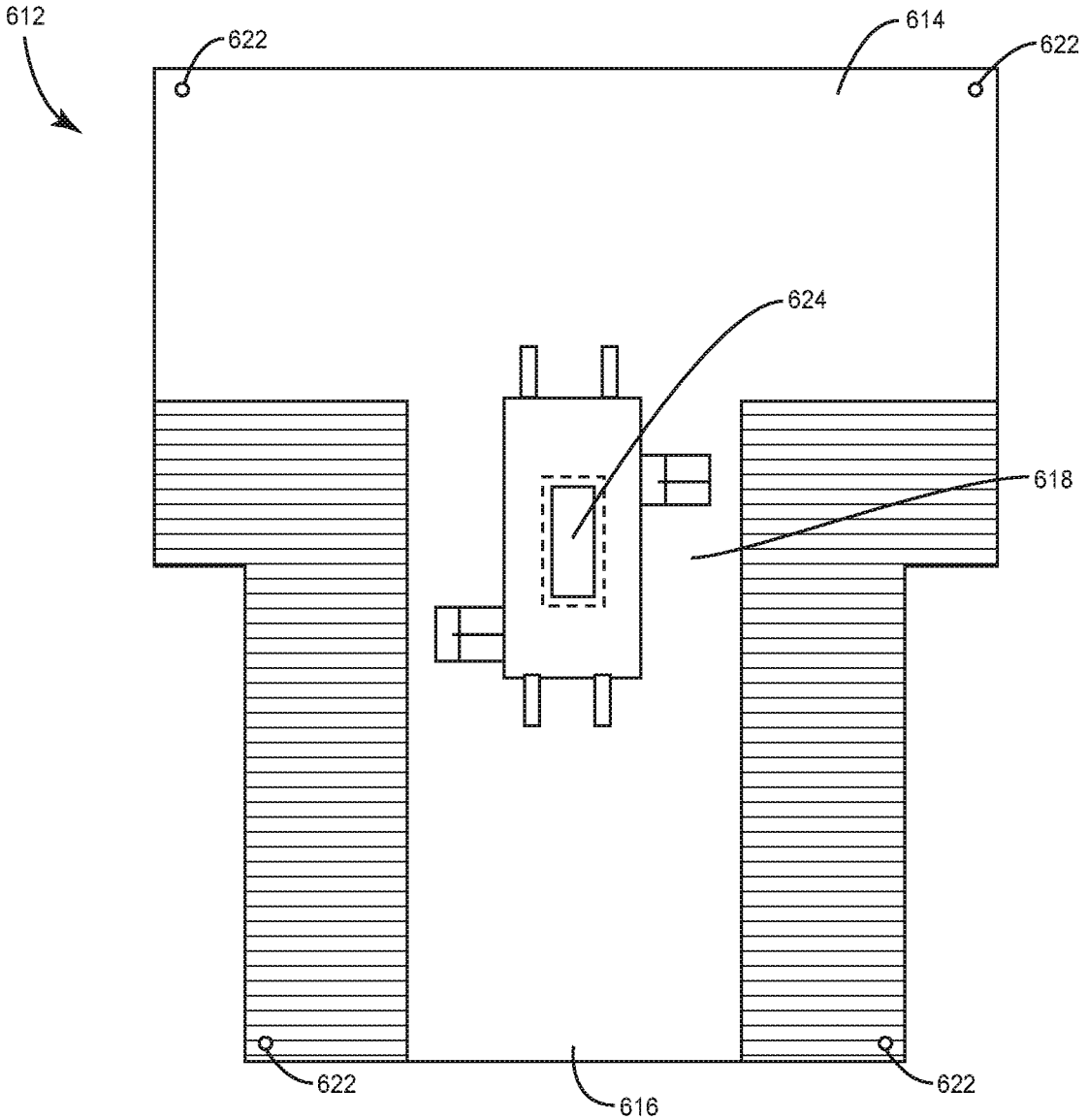
FIG. 31 is a plan view of components of one embodiment of a surgical system in accordance with the principles of the present disclosure.

In some embodiments, as shown in FIG. 31, surgical system 10, similar to the systems and methods described herein, includes a drape 612 configured for use with drapes 12, 212, 512, 712, 812, 912, as described herein. Drape 612 includes a cranial end 614, a caudal end 616 and a body portion 618. Drape 612 is configured to cover all or a portion of surgical table T and/or all or a portion of patient P. Ends 614, 616 are attached to drape poles 622 (for example, IV poles) at a head and a foot of patient P, and supported at a height above surgical table T and patient P. Portion 518 includes an opening 524 configured for alignment with the surgical site, as described herein. For example, drape 612 is applied over a fully deployed drape 12, as described herein, such that opening 624 is aligned directly over an incision and seal 14. Drape 612 is held and suspended over patient P by poles 622 such that when table T is rotated, as described herein, drape 12, which is adhered to patient P, rotates with table T and drape 612 remains stationary. Opening 624 also remains stationary and is disposed over seal 14, which corresponds to the sterile surfaces of patient P. In some embodiments, this configuration allows a surgeon to perform a procedure through opening 624 and make an incision through seal 14 when patient P is rotated into an orientation that renders accessible a selected surgical approach.

Figure 32:
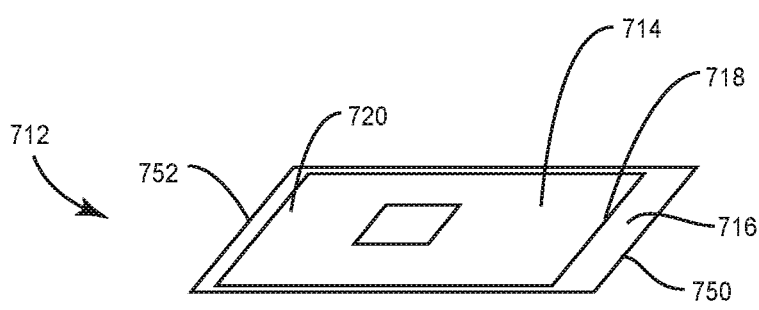
FIG. 32 is a perspective view of components of one embodiment of a surgical system in accordance with the principles of the present disclosure.
Figure 33:
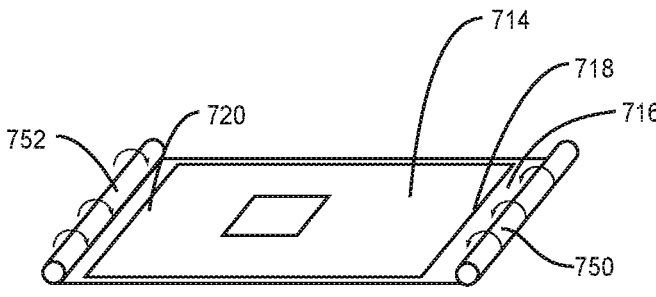
FIG. 33 is a perspective view of components of one embodiment of a surgical system in accordance with the principles of the present disclosure.
Figure 34:
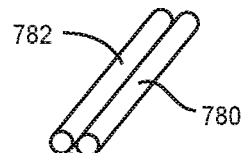
FIG. 34 is a perspective view of components of one embodiment of a surgical system in accordance with the principles of the present disclosure.
Figure 35:
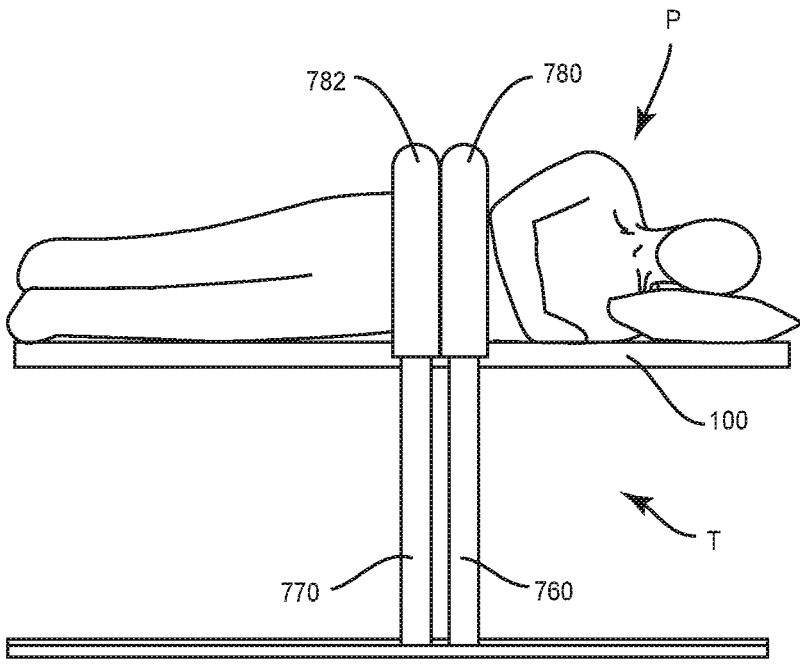
FIG. 35 is a side view of components of one embodiment of a surgical system in accordance with the principles of the present disclosure disposed with a patient body.
Figure 36:
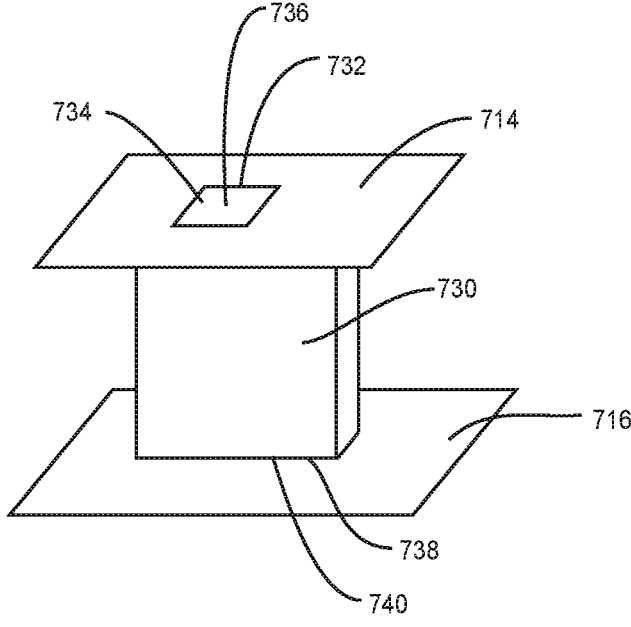
FIG. 36 is a perspective view of components of one embodiment of a surgical system in accordance with the principles of the present disclosure.
Figure 37:
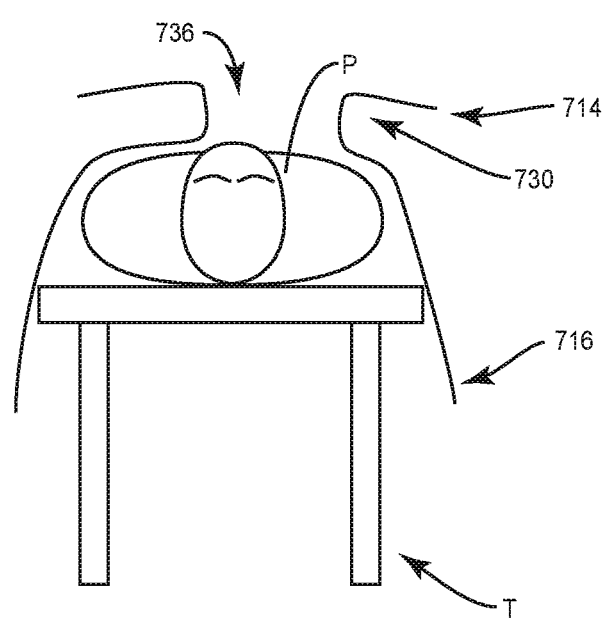
FIG. 37 is an end view of components of one embodiment of a surgical system in accordance with the principles of the present disclosure disposed with a patient body.

In some embodiments, as shown in FIGS. 32-37, surgical system 10, similar to the systems and methods described herein, includes a draping 712, similar to drape 12 described herein. Draping 712 is configured to be disposed in a non-deployed orientation, as shown in FIGS. 34 and 35, and manipulated, drawn, expanded and/or translated to a deployed orientation, as shown in FIGS. 36 and 37, for circumferential disposal about the body of patient P and/or to define a sterile region R about the body of patient P.

Draping 712 includes an over drape 714 and an under drape 716. Drape 714 extends between an end 718 and an end 720. Drape 714 includes a surface 722 that defines an opening 724. Surface 722 is configured for connection with a sleeve 730, as described herein. Drape 714 is suspended a distance over patient P upon deployment and expansion of sleeve 730, as described herein. Opening 724 is oriented for positioning relative to sterile region R. Opening 724 is in communication with a sterile surgical pathway 736 to provide access to one or more surgical approaches disposed within sterile region R during rotation of patient P using surgical table T, as described herein.

Sleeve 730 defines a wall 732. Wall 732 includes an inner surface 734 that defines a cavity, such as, for example, surgical pathway 736. Surgical pathway 736 is in communication with sterile region R and provides access to one or more incisions disposed within sterile region R. In some embodiments, sleeve 730 includes a tubular configuration. Sleeve 730 is movable and/or flexible in a plurality of orientations, such as, for example, moveable between a contracted orientation, as shown in FIGS. 32-34, and an expanded orientation, as shown in FIG. 36. Sleeve 730 is connectable between drape 714 and drape 716 to define surgical pathway 736 including a selected surface S of a body of a patient P, as described herein.

Sleeve 730 includes a seal 738 configured to seal a space between drapes 714, 716 and surface S of patient P. In some embodiments, seal 738 includes a gasket 740. Gasket 740 and sleeve 730 define a sterile boundary around a sterile region R, as described herein. Sleeve 730 is relatively movable in a plurality of orientations relative to gasket 740 to maintain sterile region R and provide access to one or more incisions disposed within sterile region R corresponding to and/or in alignment with one or more surgical approaches.

In some embodiments, sleeve 730 and gasket 740 are monolithically formed. In some embodiments, sleeve 730 is a separate component from gasket 740. In some embodiments, sleeve 730 is an integral component with gasket 740. In some embodiments, sleeve 730 is connected with gasket 740, such as, for example, with clips, hooks, adhesives and/or flanges.

In some embodiments, gasket 740 includes a flexible configuration such that gasket 740 is malleable to a selected configuration for disposal about sterile region R. In some embodiments, gasket 740 includes a surface configured for direct engagement with surface S of patient P. In some embodiments, gasket 740 includes a planar configuration to facilitate engagement with surface S. In some embodiments, gasket 740 is coated with a substrate. In some embodiments, the substrate is applied as an adhesive strip. In some embodiments, the substrate includes a pressure-sensitive material that facilitates adherence when applied to surface S. In some embodiments, gasket 740 is circumferentially adhered to the skin of patient P. Adherence of gasket 740 with surface S allows gasket 740 to rotate with the body of patient P as table T is rotated, as described herein.

Drape 716 extends between an end 750 and an end 752. Drape 716 includes a surface 754 that defines an opening 756. Surface 754 is configured for connection with sleeve 730 such that opening 756 is disposed in alignment with opening 724 and surgical pathway 736, as described herein. Drape 716 is configured for bi-directional telescopic deployment to enclose patient P and provide access to one or more selected surgical approaches in connection with surgical treatment of a spine, as described herein. In some embodiments, drape 714 includes a different dimension than drape 716, as shown in FIG. 32, for example, drape 714 is shorter than drape 716. In some embodiments, drape 714 includes a similar dimension to drape 716.

In some embodiments, drape 716 and/or drape 714 are directly connected with sleeve 730. In some embodiments, sleeve 730 is connected with drape 716 and/or drape 714, such as, for example, with clips, hooks, adhesives and/or flanges. In some embodiments, sleeve 730 and drape 716 and/or drape 714 are monolithically formed. In some embodiments, sleeve 730 is a separate component from drape 716 and/or drape 714. In some embodiments, sleeve 730 is an integral component with drape 716 and/or drape 714.

Draping 712 includes a deployment loop 760, similar to deployment loop 340 described herein, attached with ends 718, 750 and a deployment loop 770, similar to deployment loop 440 described herein, attached with ends 720, 752. Deployment loops 760, 770 are configured for connection with a surgical table, similar to surgical table T described herein.

In operation, draping 712 is configured to be disposed in a non-deployed orientation, as shown in FIG. 35, and manipulated, drawn, expanded and/or translated to a deployed orientation, as shown in FIGS. 36 and 37, for circumferential disposal about the body of patient P and/or to define a sterile region about the body of patient P. In the non-deployed orientation, draping 712 is disposed in a contracted, collapsed and/or compact configuration, as shown in FIG. 34, similar to that described with regard to drape 12. For example, end 750 is wound to meet end 718 and ends 750, 718 are wound, loaded, rotated and/or rolled to form a roll 780. End 752 is wound to meet end 720 and ends 750, 720 are wound, loaded, rotated and/or rolled to form a roll 782. Deployment loops 760, 770 are disposed about a mid-section of patient P, as shown in FIG. 35.

Roll 780 is mounted with deployment loop 760 and roll 782 is mounted with deployment loop 770, similar to that described herein, such that seal 738 is fixed with surface S and draping 712 is drawn, expanded and/or translated relative to seal 738 in a telescoping configuration during deployment. Roll 780 is translated and/or guided along deployment loop 760, similar to that described herein, such that roll 780 facilitates circumferentially enclosing patient P and defining sterile region R. Roll 782 is translated and/or guided along deployment loop 770, similar to that described herein, such that roll 782 facilitates circumferentially enclosing patient P and defining sterile region R. In some embodiments, loop 760 and loop 770 are individually and/or separately slidable in a cranial direction and/or a caudal direction from a mid-section of patient P.

Seal 738 is positioned over the surgical site and adhered to surface S of patient P. With seal 738 fixed with surface S, deployment loop 760 is translated from the mid-section of patient P, relative to patient P and along surgical table T. In some embodiments, deployment loop 760 is translated in a cranial direction. Such translation of deployment loop 760 relative to patient P dispenses draping 712 from roll 780 away from seal 738 to draw, expand and/or translate draping 712 circumferentially about patient P. Deployment loop 770 is translated from the mid-section of patient P in a direction opposite to that of deployment loop 760, relative to patient P and along surgical table T. In some embodiments, deployment loop 770 is translated in a caudal direction. Such translation of deployment loop 770 relative to patient P dispenses draping 712 from roll 782 away from seal 738 to draw, expand and/or translate draping 712 circumferentially about patient P.

As draping 712 is translated and dispensed circumferentially about patient P, drapes 714, 716 are similarly disposed about patient P with sleeve 730 disposed between drapes 714, 716 in a contracted orientation. Upon deployment of draping 712, drape 714 is lifted, pulled and/or drawn away from drape 716 to dispose sleeve 730 in an expanded orientation, as shown in FIGS. 36 and 37. Drapes 714, 716 are spaced apart adjacent sleeve 730 to define surgical pathway 736 and provide access to a surgical site for performing a surgical procedure, similar to that described herein. During rotation of the patient P and drape 716, sleeve 730 articulates to maintain access to the surgical site or sites via the surgical pathway 736.

In some embodiments, as shown in FIGS. 38-41, surgical system 10, similar to the systems and methods described herein, includes a draping 812, similar to drape 12 described herein. Draping 812 is configured to be disposed in a non-deployed orientation and manipulated, drawn, expanded and/or translated to a deployed orientation for circumferential disposal about the body of patient P and/or to define a sterile region R about the body of patient P, as described herein.

Draping 812 includes an over drape 814 and an under drape 816. Drape 814 extends between an end 818 and an end 820. Drape 814 includes a surface 822 that defines an opening 824. Surface 822 is configured for connection with a sleeve 830, as described herein. Opening 824 is oriented for positioning relative to sterile region R. Opening 824 is in communication with a surgical pathway 836 to provide access to one or more surgical approaches disposed within sterile region R during rotation of patient P using surgical table T, as described herein.

Figure 41:
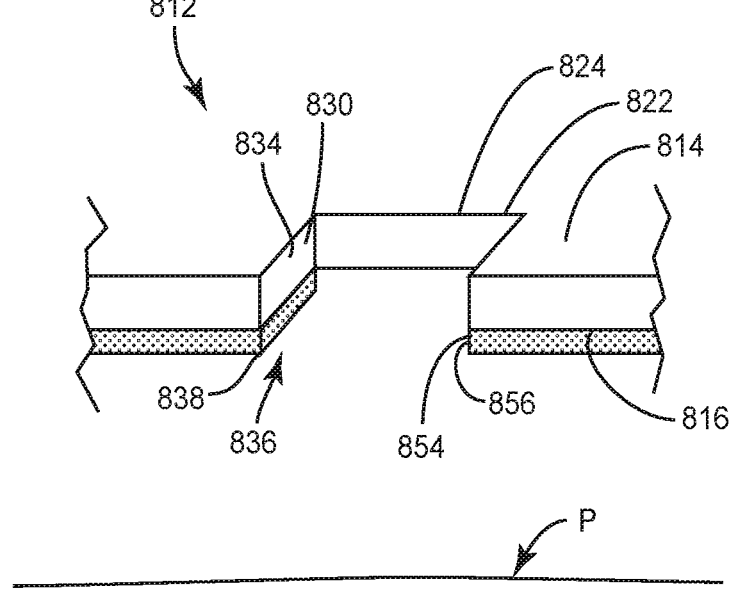
FIG. 41 is a break away, cross section view of components of one embodiment of a surgical system in accordance with the principles of the present disclosure.

Drape 814 includes sleeve 830. Sleeve 830 defines a wall 832. Wall 832 includes an inner surface 834 that defines a surgical pathway 836, as shown in FIG. 41. Surgical pathway 836 is in communication with sterile region R and provides access to one or more incisions disposed within sterile region R. In some embodiments, sleeve 830 includes a tubular configuration. Drape 814 is configured for bi-directional telescopic deployment to enclose patient P and provide access to one or more selected surgical approaches in connection with surgical treatment of a spine, as described herein.

In some embodiments, sleeve 830 is an integral component with drape 814. In some embodiments, sleeve 830 and drape 814 are monolithically formed. In some embodiments, sleeve 830 is a separate component from drape 814. In some embodiments, sleeve 830 is connected with drape 814, such as, for example, with clips, hooks, adhesives and/or flanges.

Drape 816 extends between an end 850 and an end 852. Drape 816 includes a surface 854 that defines an opening 856. A seal 838, similar to seal 738 as described herein, is connected with surface 854 about opening 856 for adherence to a surface of patient P. Surface 854 is configured for connection with sleeve 830 such that opening 856 is disposed in alignment with opening 824 and surgical pathway 836, as described herein. Drape 816 is configured for bi-directional telescopic deployment to enclose patient P and provide access to one or more selected surgical approaches in connection with surgical treatment of a spine, as described herein. Drape 816 is connected with sleeve 830. In some embodiments, sleeve 830 is connected with drape 816, such as, for example, with clips, hooks, adhesives and/or flanges.

Drape 814 includes a deployment loop 860, similar to deployment loop 340 described herein, attached with end 818 and a deployment loop 870, similar to deployment loop 440 described herein, attached with end 820. Deployment loops 760, 770 are configured for connection with a surgical table, similar to surgical table T described herein.

Drape 818 includes a deployment loop 860a, similar to deployment loop 340 described herein, attached with end 850 and a deployment loop 870b, similar to deployment loop 440 described herein, attached with end 852. Deployment loops 760a, 770a are configured for connection with a surgical table, similar to surgical table T described herein.

In operation, seal 838 is adhered to a surface of patient P. With seal 838 disposed about opening 856, drape 816 is disposed in a non-deployed orientation such that drape 816 is disposed in a contracted, collapsed and/or compact configuration, as described herein. For example, end 850 is wound, loaded, rotated and/or rolled to form a roll, as described herein. End 752 is wound, loaded, rotated and/or rolled to form a roll, as described herein. Deployment loops 860a, 870a are disposed about a mid-section of patient P. Drape 816 is mounted with deployments loops 860a, 870a, as described herein. Drape 816 is drawn, expanded and/or translated in a telescoping configuration during deployment, similar to that described herein, such that drape 816 circumferentially encloses patient P and defines sterile region R, as described herein.

Figure 38:
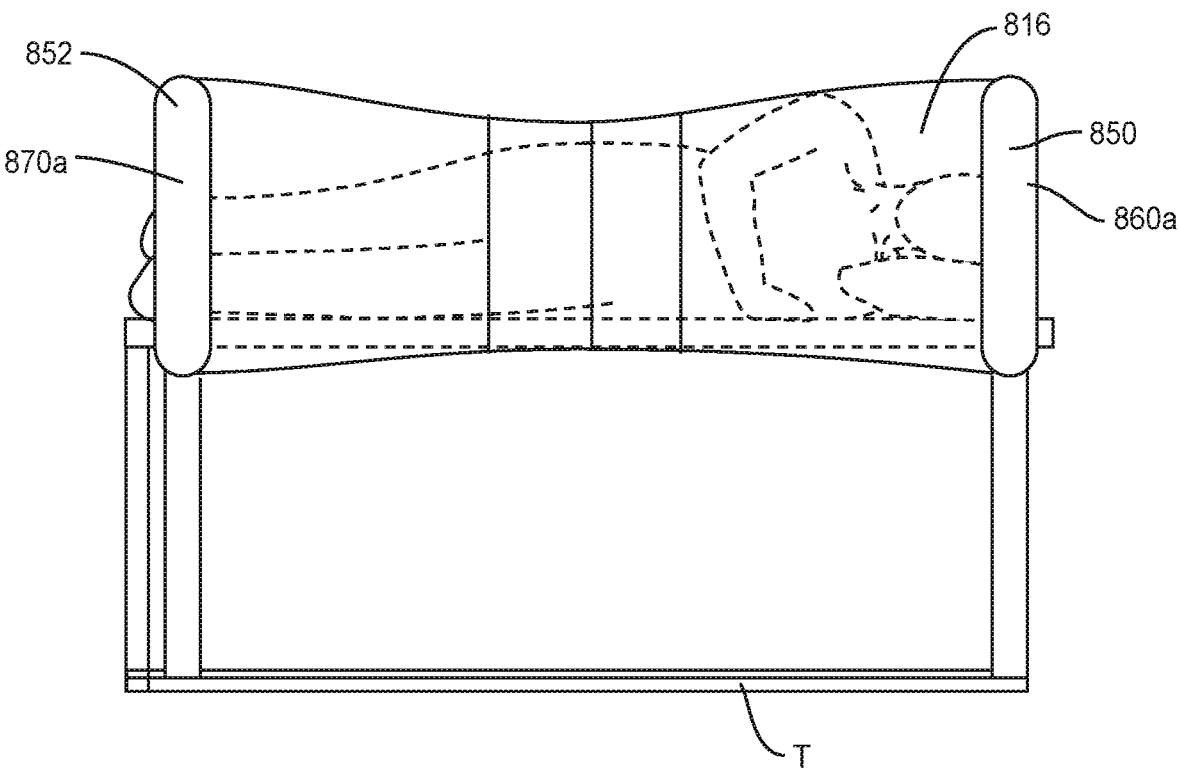
FIG. 38 is a side view of components of one embodiment of a surgical system in accordance with the principles of the present disclosure.
Figure 39:
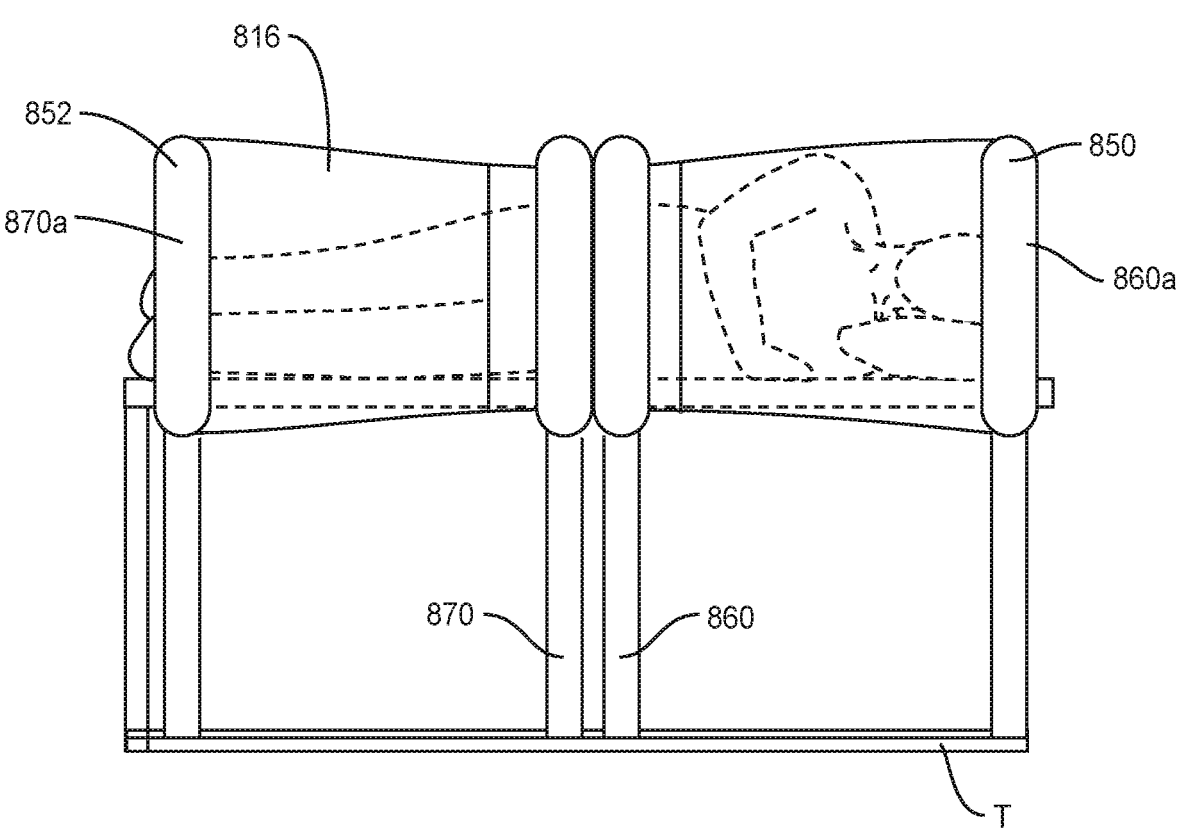
FIG. 39 is a side view of the components shown in FIG. 38.
Figure 40:
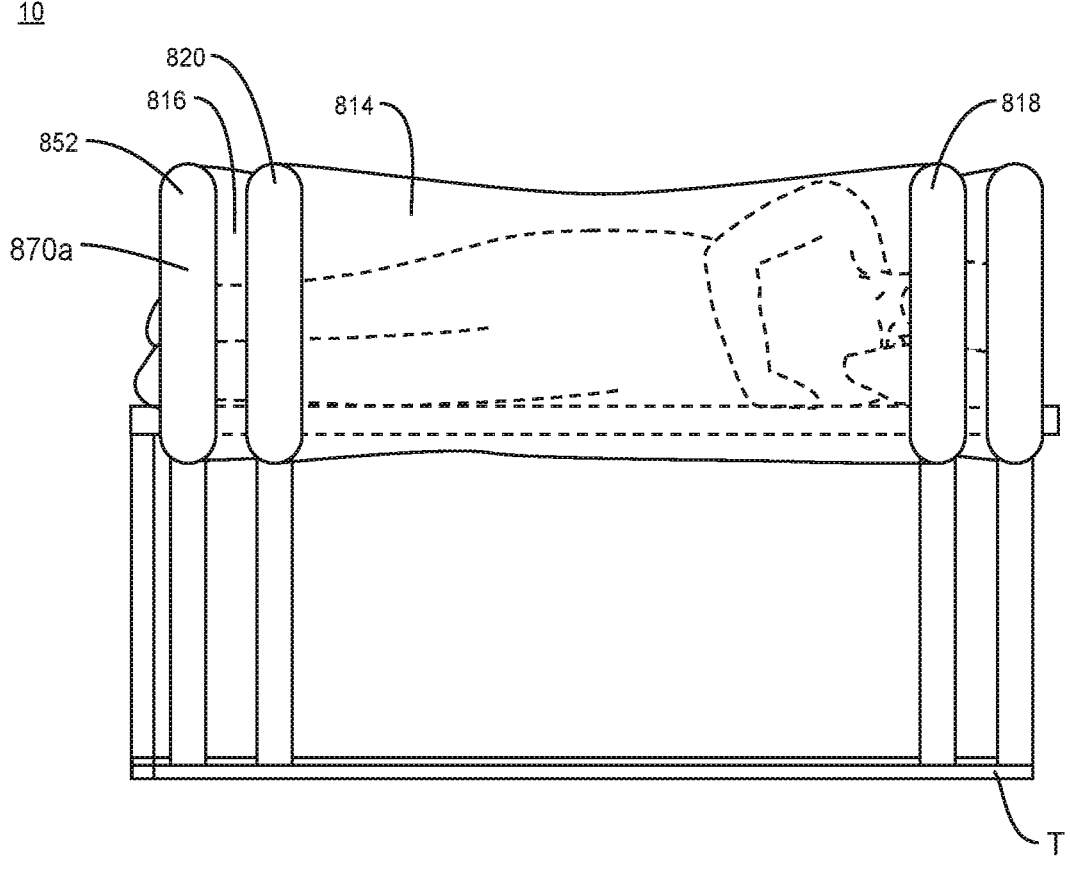
FIG. 40 is a side view of the components shown in FIG. 38.

Drape 814 is configured to be disposed in a non-deployed orientation and manipulated, drawn, expanded and/or translated to a deployed orientation, as shown in FIGS. 40 and 41, for circumferential disposal about the body of patient P and/or to define a sterile region about the body of patient P. For example, end 818 is wound, loaded, rotated and/or rolled to form a roll, as described herein. End 820 is wound, loaded, rotated and/or rolled to form a roll, as described herein. Deployment loops 860, 870 are disposed about a mid-section of patient P. Drape 814 is mounted with deployments loops 860, 870, as described herein. Drape 814 is drawn, expanded and/or translated in a telescoping configuration during deployment, similar to that described herein, such that drape 814 circumferentially encloses drape 816 and patient P and defines sterile region R, as described herein. As drape 814 is translated, sleeve 830 expands to define surgical pathway 836 between drapes 814, 816, as shown in FIG. 38.

Drapes 814, 816 are spaced apart adjacent sleeve 830 to define surgical pathway 836 and provide access to a surgical site for performing a surgical procedure, similar to that described herein. During rotation of the patient P and drape 716, sleeve 730 articulates to maintain access to the surgical site or sites via the surgical pathway 736. Surgical pathway 836 is in communication with sterile region R and provides access to one or more incisions disposed within sterile region R.

Figure 42:
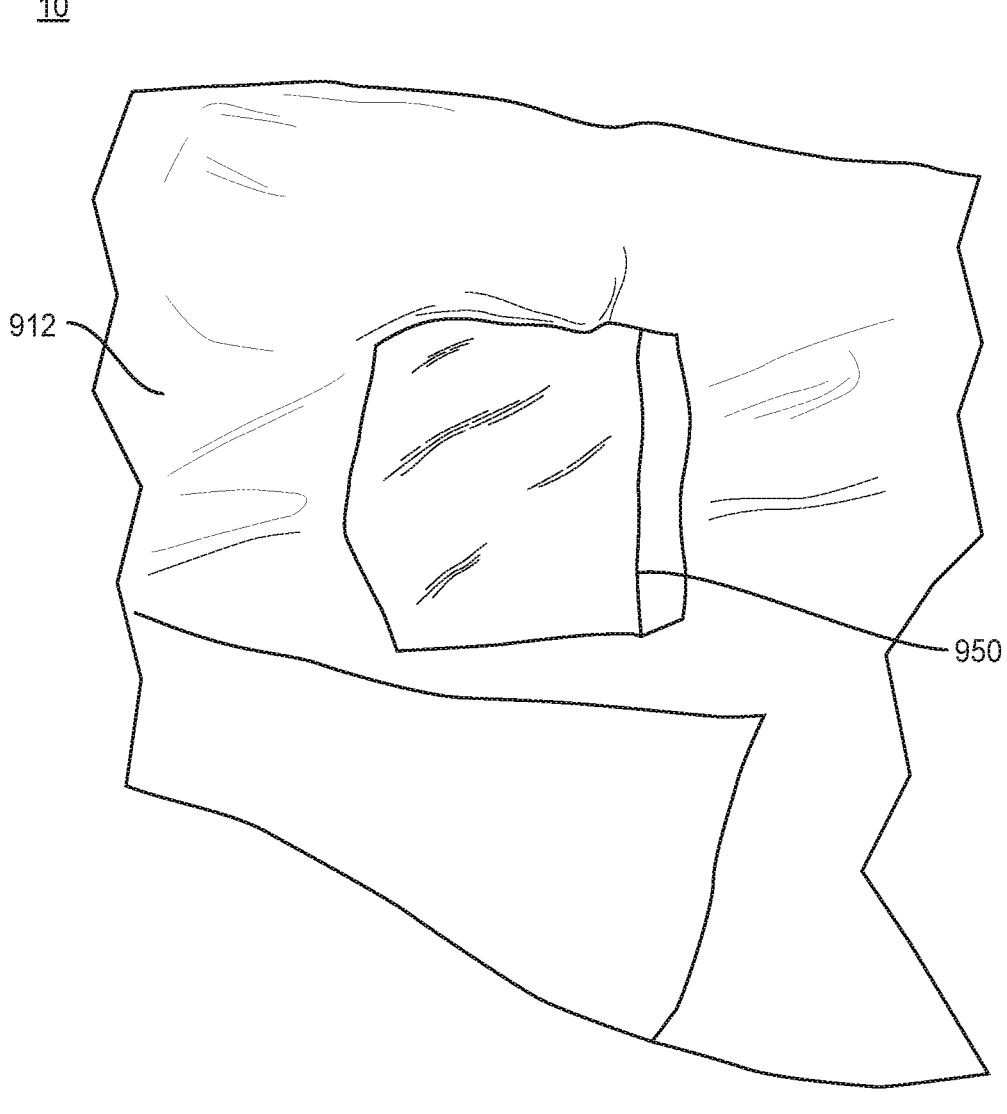
FIG. 42 is a plan view of components of one embodiment of a surgical system in accordance with the principles of the present disclosure.

In some embodiments, as shown in FIG. 42, surgical system 10, similar to the systems and methods described herein, includes a drape 912, similar to drape 12 described herein. In some embodiments, drape 912 includes one or a plurality of pockets 950 attached thereto. In some embodiments, pocket 950 includes a transparent material. In some embodiments, pocket 950 can be used to store various surgical materials and/or instruments during surgery. In some embodiments, pocket 950 is configured to hold an electronic and/or remote control for a surgical table. In some embodiments, pocket 950 is configured to facilitate access to table controls by practitioners to manipulate the controls without breaking sterility. In some embodiments, surgical tables are operated by a handheld remote control that is connected to the table via a cord that is generally non-sterile. In some embodiments, pocket 950 positions a remote control beneath the sterile field where its buttons can be pressed easily through the drape. In some embodiments, pocket 950 is configured to facilitate connection with other devices by touch screen and/or a wireless link, such as, for example, Bluetooth, NFC, Wi-Fi, MICS. In some embodiments, pocket 950 is configured for disposal of a mobile digital device, for example, an iPad® control screen for pressure measurements and/or for communication between other devices in the operating room, such as, for example, x-rays, C-arms, fluoroscopy, O-arm and/or navigation technology.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical drape system comprising:
   a surgical table comprising a rotatable first platform having a surface configured to support a body of a patient, the surface of the first platform extending between a first end and an opposite second end of the first platform, the first platform being supported spaced from a floor by a pedestal at the first end of the first platform, the surgical table comprising a base that engages the floor, the pedestal connecting the base with the first platform, and the base comprising a track;

a first loop and a second loop each being movably connected with the track, the first and second loops being configured to move relative to one another and to the first platform, the first loop being moveable from a first position adjacent the second loop to a second position adjacent the first end of the first platform, and the second loop being moveable from a third position adjacent the first loop to a fourth position adjacent the second end of the first platform;

an over-draping including a first over-draping portion initially rolled around portions of the first loop and a second over-draping portion initially rolled around portions of the second loop; and a seal connectable with a selected surface of the body, the seal including a first end coupled to the first over-draping portion, and an opposite second end coupled to the second over-draping portion;

wherein movement of the first loop from the first position to the second position unfurls the first over-draping portion from a first non-deployed orientation to a first deployed orientation to define with the seal a first sterile region about a first portion of the body, and movement of the second loop from the third position to the fourth position unfurls the second over-draping portion from a second non-deployed orientation to a second deployed orientation to define with the seal a second sterile region about a second portion of the body; and wherein the first over-draping portion and the second over-draping portion are hung from the corresponding first and second loops to maintain portions thereof at positions above the body to allow the first platform to rotate while simultaneously maintaining the first sterile region and the second sterile region, and maintaining access to the seal.

2. The surgical drape system of claim 1, further comprising an under-draping including a first under-draping portion positioned directly on the first portion of the body and attached relative to the seal, and a second under-draping portion positioned directly on the second portion of the body and attached relative to the seal.

3. The surgical drape system of claim 2, further comprising a sleeve extending between the over-draping and the under-draping adjacent the seal, the sleeve enclosing an area between the over-draping and the under-draping, and defining a sterile surgical pathway to the seal.

4. The surgical drape system of claim 3, wherein the sterile surgical pathway to the seal can be maintained during rotation of the first platform to provide access via one or more surgical approaches.

5. The surgical drape system of claim 4, wherein an incision can be provided in the seal to access a surgical site on the body through the sterile surgical pathway.

6. The surgical drape system recited in claim 1, wherein the first loop is movable relative to the body in a first direction and the second loop is movable relative to the body in a second direction.

7. The surgical drape system recited in claim 6, wherein movement of the first loop in the first direction is in a cranial direction and movement of the second loop in the second direction is in a caudal direction from a mid-section of the body.

8. The surgical drape system recited in claim 1, wherein the first loop is translatable relative to the track in a first direction and the second loop is translatable relative to the track in an opposite second direction.

9. The surgical drape system recited in claim 8, wherein the first and second loops are movably connected with the track by corresponding first and second posts that are slidable along the track.

10. A surgical drape system comprising:

a surgical table comprising a rotatable first platform having a surface configured to support a body of a patient, the surface of the first platform extending between a first end and an opposite second end of the first platform, the first platform being spaced from a floor by a pedestal at the first end of the first platform, the surgical table comprising a base that engages the floor, the pedestal connecting the base with the first platform, and the base comprising a track;

a first deployment loop and a second deployment loop, the first and second deployment loops being movably connected with the track, the first and second deployment loops being each configured to move between a first position and a second position relative to the body;

a drape including an over-draping, an under-draping, and a sleeve coupled between the over-draping and the under-draping, the over-draping including a first over-draping portion initially wound around the first deployment loop and a second over-draping portion initially would around the second deployment loop, and the under-draping including a first under-draping portion and a second under-draping portion; and a seal connectable with a selected surface of the body, the seal having a first end coupled relative to the first over-draping portion and the first under-draping portion, and an opposite second end coupled relative to the second over-draping portion and the second under-draping portion;

wherein the first under-draping portion is contactable to a first portion of the body, the second under-draping portion is contactable to a second portion of the body, the first over-draping portion is unrollable via movement of the first deployment loop from the corresponding first position to the second position thereof to define a first sterile region, the second over-draping is unrollable via movement of the second deployment loop from the corresponding first position to the second position thereof to define a second sterile region, and the sleeve provides access to the seal therethrough; and wherein the first over-draping portion and the second over-draping portion are hung from the corresponding first and second loops to maintain portions thereof at positions above the body to allow the first platform to rotate while simultaneously maintaining the first sterile region and the second sterile region and maintaining access to the seal through the sleeve portion.

11. The surgical drape system of claim 10, wherein the sleeve encloses an area between the over-draping and the under-draping, and defines a sterile surgical pathway to the seal.

12. The surgical drape system of claim 11, wherein the sterile surgical pathway to the seal can be maintained during rotation of the first platform to provide access via one or more surgical approaches.

13. The surgical drape system of claim 12, wherein an incision can be provided in the seal to access a surgical site on the body through the sterile surgical pathway.

14. The surgical drape system recited in claim 10, wherein the first deployment loop is translatable relative to the track of the surgical table in a first direction relative to the body and the second deployment loop is translatable relative to the track in an opposite second direction relative to the body.

15. The surgical drape system recited in claim 10, wherein each of the first and second deployment loops are movably connected with the track by corresponding first and second posts that are slidable along the track.

16. The surgical drape system recited in claim 10, wherein the first loop is movable relative to the body in a first direction and the second loop is movable relative to the body in a second direction.

17. The surgical drape system recited in claim 10, wherein movement of the first loop in the first direction is in a cranial direction and movement of the second loop in the second direction is in a caudal direction from a mid-section of the body.

18. A surgical drape system comprising:

a surgical table comprising a rotatable first platform having a top surface configured to support a body of a patient, the surface of the first platform extending between a first end and an opposite second end of the first platform, the first platform being spaced from a floor by a pedestal at the first end of the first platform, the surgical table comprising a base that engages the floor, the pedestal connecting the base with the first platform, and the base comprising a track;

a first loop and a second loop each being moveably connected to the track, the first and second loops being moveable relative to one another and to the first platform, the first loop being moveable away from the second loop and toward the first end of the first platform, and the second loop being moveable away from the first loop and toward the second end of the first platform;

a drape including an over-draping, an under-draping, and a sleeve extending between the over-draping and the under-draping, the over-draping including a first over-draping portion initially rolled on the first loop and a second over-draping portion initially rolled on the second loop, and the under-draping including a first under-draping portion and a second under-draping portion; and a seal having a first end coupled relative to the first over-draping portion and the first under-draping portion, and an opposite second end directly coupled relative to the second over-draping portion and the second under-draping portion the seal being connectable with a selected surface of the body;

wherein the first under-draping portion and the second under-draping portion are contactable to the body, the first over-draping portion is unrollable over the first under-draping portion via movement of the first loop to define a first sterile region, the second over-draping portion is unrollable over the second under-draping portion via movement of the second loop to define a second sterile region, and the sleeve provides access to the seal therethrough; and wherein the first over-draping portion and the second over-draping portion are hung from the corresponding first and second loops to maintain portions thereof at positions above the body to allow the first platform to rotate while simultaneously maintaining the first sterile region and the second sterile region and maintaining access to the seal through the sleeve portion.

19. The surgical drape system of claim 18, wherein the sleeve encloses an area between the over-draping and the under-draping, and defines a sterile surgical pathway to the seal.

20. The surgical drape system of claim 19, wherein the sterile surgical pathway to the seal can be maintained during rotation of the first platform to provide access via one or more surgical approaches.

* * * * *